US007045788B2

(12) United States Patent
Iwatschenko-Borho et al.

(10) Patent No.: US 7,045,788 B2
(45) Date of Patent: May 16, 2006

(54) MULTI-WAY RADIATION MONITORING

(75) Inventors: Michael Iwatschenko-Borho, Erlangen (DE); Norbert Trost, Erlangen (DE); Bernd Friedrich, Erlangen (DE)

(73) Assignee: Thermo Electron Corporation, Waltham, MA (US)

( * ) Notice: Subject to any disclaimer, the term of this patent is extended or adjusted under 35 U.S.C. 154(b) by 331 days.

(21) Appl. No.: 10/663,417

(22) Filed: Sep. 16, 2003

(65) Prior Publication Data
US 2005/0029460 A1 Feb. 10, 2005

Related U.S. Application Data

(60) Provisional application No. 60/492,429, filed on Aug. 4, 2003.

(51) Int. Cl.
*G01T 1/167* (2006.01)
(52) U.S. Cl. .................. 250/359.1; 250/358.1; 250/394; 250/361 R; 250/366
(58) Field of Classification Search ............ 250/359.1, 250/358.1, 361 R, 366
See application file for complete search history.

(56) References Cited

U.S. PATENT DOCUMENTS

| | | | | |
|---|---|---|---|---|
| 5,330,142 A | * | 7/1994 | Gnau, III | 248/124.1 |
| 5,679,956 A | | 10/1997 | Johnston et al. | |
| 5,705,818 A | * | 1/1998 | Kelbel et al. | 250/361 R |
| 6,031,890 A | * | 2/2000 | Bermbach et al. | 378/57 |
| 6,708,140 B1 | * | 3/2004 | Zerwekh et al. | 702/188 |
| 6,727,506 B1 | * | 4/2004 | Mallette | 250/394 |
| 6,937,692 B1 | * | 8/2005 | Johnson et al. | 378/57 |
| 2002/0092988 A1 | * | 7/2002 | Didomenico et al. | 250/338.5 |
| 2003/0226971 A1 | * | 12/2003 | Chandross et al. | 250/361 R |

FOREIGN PATENT DOCUMENTS

| | | |
|---|---|---|
| GB | 2158572 | 11/1985 |
| WO | WO 00/26641 | 5/2000 |

* cited by examiner

*Primary Examiner*—Albert Gagliardi
(74) *Attorney, Agent, or Firm*—Chapin IP Law, LLC; Barry W. Chapin, Esq.

(57) ABSTRACT

A multi-way radiation monitoring and detection system is capable of detecting a radiation source on or within traffic that can travel within M adjacent traffic ways, where M is an integer equal to or greater than a value of 2. The radiation detection system comprises a set of (M+1) radiation detector assemblies with individual radiation detector assemblies of the set of (M+1) radiation detector assemblies respectively positioned at each of two sides of each of the M adjacent traffic ways. A set of M controllers is included and each controller is associated with a respective traffic way of the M adjacent traffic ways. Each controller is coupled to the respective individual radiation detector assemblies positioned at the two sides of the traffic way to which that controller is associated, such that two controllers associated with two adjacent traffic ways couple to the individual radiation detector assembly positioned between those two adjacent traffic ways. Each controller is operable to receive a radiation signal produced from at least one radiation detector assembly coupled to that controller to identify a radiation source present in a traffic way adjacent to the at least one radiation detector assembly. Some of the detectors within detector assemblies between traffic ways may be unshielded plastic Gamma radiation detectors, with such detector assemblies or associated controllers having natural background radiation rejection processors.

35 Claims, 13 Drawing Sheets

MULTI-WAY RADIATION MONITORING

CLAIM TO BENEFIT OF EARLIER FILED U.S. PROVISIONAL APPLICATION

This utility patent application claims the benefit of the filing date of earlier filed U.S. Provisional Patent Application entitled "MULTI-WAY RADIATION MONITORING" filed Aug. 4, 2003 having U.S. Ser. No. 60/492,429. This utility patent application shares co-inventorship with this referenced Provisional Patent Application and is assigned to the same assignee. The entire contents of this referenced Provisional Patent Application are hereby incorporated herein by reference in its entirety.

BACKGROUND

Due to growing worldwide concerns about the proliferation and possible smuggling or other transport of radioactive nuclear materials across borders of states and countries, governments of several nations have recently requested and commissioned the installation of radioactivity monitors at a large number of international border crossing locations.

A design of one type of conventional radiation detection system (further referenced herein as radiation detection system type A) located at a border crossing point, such as a highway that intersects two adjoining countries, includes a respective dedicated pair of radiation detector assemblies positioned on each side of each lane of the highway. Each radiation detector assembly pair for each lane includes two Gamma radiation detectors that are shielded with a radiation shield on the backsides of both Gamma detectors (i.e., the sides of the Gamma detectors that face away from the lane which those detectors monitor) in order to shield the detectors from ambient or background radiation that may affect the accuracy of the detector in detecting a radiation source within the lane associated with those detectors. The shielding also minimizes the influence of radiation variations caused by vehicle induced shielding of the background radiation by vehicles in neighboring lanes that pass adjacent to a detector assembly. The shielding on the backsides of the detector pairs associated with a particular lane of the highway may be, for example, lead plates (typically 1 cm or less in thickness) or steel panels or other radiation absorbing materials disposed respectively upon each detector assembly.

Each lane in such a conventional system design thus requires two shielded radiation detectors dedicated specifically to detecting radiation sources within that lane. If two lanes are adjacent to one another, the two shielded detectors positioned between the adjacent lanes can be arranged in a back-to-back configuration such that the shielding of the two detectors faces each other. In an alternative conventional configuration, opposing shielded detectors positioned between adjacent lanes are arranged side-by-side such that the unshielded front side (i.e., the radiation detecting side) of one detector for one lane is parallel or flush with a shielded backside of the other detector for the other adjacent lane. The side-by-side configuration consumes somewhat less real estate in the cross-lane direction and is useful in situations where there is not much area to provide for installation of such systems. Regardless of the configuration, each lane in this conventional design requires the use of two separately shielded radiation detectors in order to adequately detect a radiation source within that lane.

The radiation detector pairs for each lane in a conventional system design are coupled to a controller device that receives radiation detection signals from the detectors in that lane in order to process such signals and, optionally, to notify a central computer system in the event that one or both detectors in any particular lane detect a radiation source traveling within that lane. The central computer system can be located, for example, within a tollbooth, border crossing or customs station located downstream from the traffic flow of the lane with respect to the radiation detection system. As an example, the radiation detection system may be placed 100 or more meters ahead of a border crossing station. In this manner, as a car, truck or other vehicle traveling in lane transports a radiation source through a detector pair associated with that lane, the radiation source within the vehicle activates one or both of the detectors for that lane. In response, the controller coupled to the activated detector can notify an operator directly or through the central computer system in order to stop the vehicle at the customs station or tollbooth for further inspection in order to determine the legitimacy of the radiation source being transported by the vehicle.

Another radiation detection system design (further referenced herein as radiation detection system type B) uses a single radiation detector disposed between adjacent lanes of a multilane highway. The outer lanes of the highway are flanked on each outer edge with a single detector as well. All of the single detectors in this alternative configuration are coupled to a common controller or central computer system that notifies an operator of the trafficking of radiation within the lanes in the event a vehicle carrying a radiation source passes one of the detectors.

SUMMARY

Conventional radiation detector system designs that monitor the transport of radiation within travel ways such as lanes of a highway suffer from a variety of deficiencies. In particular, most conventional designs of such radiation detection systems (e.g., type A systems) utilize dual back-to-back shielded detector assemblies that are largely duplicative in construction and operation for detection of radiation sources between adjacent lanes or traffic ways. In particular, such radiation detector system designs call for two radiation detectors placed into different housings that are each shielded from background radiation effects in a direction of radiation detection of the other detector assembly disposed in the back-to-back configuration. As a result of this design, significant expenses are incurred in terms of system cost and installation overhead due to the requirement of providing separate stanchions, housings, detectors, electrical components, and shielding for each of the two shielded detector assemblies required to be positioned between the adjacent lanes.

As an example, for an application on a highway having two lanes, four detector assemblies are required, two for each lane, with the detector assemblies containing shielding to protect the radiation detector from background radiation and, for the two center detector assemblies, to protect the detectors from vehicle shielding effects encountered from a direction of the adjacent lane for which that detector assembly is not responsible for monitoring or detecting a radiation source. To generalize this inefficiency with type A radiation detector system designs, the general number N of required radiation detector assemblies for an M-lane highway is given by the formula:

$$N = 2 * M.$$

In systems that require significant coverage areas of detection (e.g., to monitor tall vehicles such as large trucks), the number of components may increase by a factor of P, where P is a multiple indicating how many detector assemblies are to be positioned on top of one another to obtain the desired height requirement. In such cases, the number of detectors required is given by the formula:

$$N=2*M*P$$

In the alternative design (e.g., type B) that utilizes a single detector assembly in between adjacent lanes, all detector assemblies are coupled to a common controller and are typically treated as a single unit, so an alarm, when generated, does not indicate which specific lane contains the radiation source. By way of example, in a two-lane highway application, only three detector assemblies are required to monitor traffic in both lanes using this design. However, since all three detectors couple to a single individual controller, failure of the controller means failure of the whole system—i.e., no fault tolerance.

Indeed, both of the above-described radiation detection system designs suffer from a lack of fault tolerance in the event of component failure. As an example, in the aforementioned type A design that uses back-to-back shielded radiation detectors positioned between adjacent lanes, since the controllers in such systems only couple to the detector pairs responsible for monitoring a particular lane associated with that controller, in the event of failure of either one of the detectors or of the controller itself, that lane of the highway is insufficiently capable of detecting a radiation source. In particular, if one of the radiation detectors experiences a failure, the controller may or may not be aware of the failure and may continue to operate with the assumption that both detectors are functioning properly. If a vehicle transporting a radiation source contains that radiation source in a position within the vehicle on the side of the lane closest to the failed detector, when the vehicle passes through the radiation detection system, there is a likelihood that the still functioning detector on the opposite side of the lane may be incapable of detecting the radiation source. This may be due to shielding effects of the portion of the vehicle positioned between the radiation source and the still functioning detector. In effect, a failed detector that is unbeknownst to a controller may cause a gap in coverage of the radiation detection system. Furthermore, if the controller itself fails in a type A system design, the entire lane becomes unusable and traffic flow must be diverted or rerouted to other lanes.

In known radiation detector system designs that utilize a single detector disposed between adjacent lanes (i.e., type B systems), since all detectors are coupled to a common controller, in the event of failure of the common controller the entire radiation detection system may fail to operate properly.

Embodiments of the invention significantly overcome these and other deficiencies associated with known designs of radiation detection systems of both type A and type B utilized to detect the transport of radiation sources on or within vehicles, persons, or other items traveling in traffic ways. Embodiments of the invention provide radiation detection systems that are, or achieve, on or more of the following: simpler to install, more redundant in the event of failure of a component within the system, have improved performance, and cost significantly less due to a decrease in the required componentry as compared with previously known systems.

In particular, embodiments of the invention provide a radiation detection system capable of detecting a radiation source within traffic such as any vehicle that can travel within multiple adjacent traffic ways, lanes, paths, travel routes, etc. As an example, for a setting in which there are M adjacent traffic ways, where M is an integer equal to or greater than two, the system of the invention includes a set of (M+1) radiation detector assemblies respectively positioned at each of two sides of each of the M adjacent traffic ways. Each radiation detector assembly positioned between adjacent traffic ways or lanes in embodiments of the invention may not include shielding and is thus operable to detect radiation from a radiation source in either of the two adjacent lanes adjoining that radiation detector assembly. The two radiation detector assemblies on the outermost side of each outermost lane preferably contain shielding, though this is not essential to the invention.

The system further includes a set of M controllers, and each controller is associated with a respective traffic way of the M adjacent traffic ways. As an example, for a highway there is one controller for each lane. Each controller is coupled to (i.e., is capable of communication with) the respective individual radiation detector assemblies positioned at the two sides of the traffic way or lane to which that controller is associated. Thus, according to the design of embodiments of the invention, two controllers associated with two adjacent traffic ways couple to the individual radiation detector assembly positioned between those two adjacent traffic ways. The controllers are operable to receive radiation signals from the radiation detector assemblies coupled to that controller and to identify a radiation source present in at least one of the traffic ways adjacent to a radiation detector assembly.

Redundancy is provided in the design of the embodiments of the invention since the controllers operate independently of each other and each controller is coupled to a detector assembly shared with another controller. If one controller experiences a failure, at least one non-failed controller associated with at least one traffic way adjacent to a traffic way associated with the failed controller (i.e., neighboring controllers that are also coupled to the same radiation detector assemblies as the failed controller) is/are operable to receive a radiation signal produced from the individual radiation detector assembly coupled to both the non-failed controller and the failed controller. In one configuration, a vehicle traffic sensor is wired to both neighboring lane controllers so that these controllers can receive a signal from the traffic sensor in neighboring lanes in addition to being coupled to the detector shared between the two lanes. In this manner, one controller is able to fully replace a defective controller without any service intervention.

Embodiments of the invention can further include a central computer system in communication with the set of M controllers to receive controller output signals from each controller. The controller output signal from a controller provides a measurement of radiation associated with each radiation detector assembly coupled to that controller, including radiation from a non-natural source detected by a radiation detector coupled to that controller. The controller output signal can also include an identity of the radiation detector that detected the radiation source. The central computer system processes the controller output signals from each controller to make a determination of which traffic way of the M adjacent traffic ways contains the radiation source. In some embodiments, the controller output signals from each controller provide an adjusted level of radiation detected by the radiation detector assemblies coupled to that controller and an identity of the radiation detector assembly associated with the adjusted level of radiation. The central computer system is operable to correlate the adjusted levels of radiation from a plurality of radiation detector assemblies to identify patterns of correlated levels of radiation that indicate the existence of a radiation source within a specific traffic way of the M adjacent traffic ways. As an example, if multiple traffic ways have a vehicle present between detectors during a detection of a radiation source, multiple controllers may alarm if a radiation source is quite strong. In such cases, the central computer can suppress the alarms of those controllers that associated with detectors that indicate weaker signals.

In certain embodiments a common Neutron detector is shared—i.e., some of the radiation detector assemblies lack a Neutron detector. In that case, interaction of vehicles from other lanes need not be considered nor is shielding an issue. Care must, however, be taken that the geometry of the surrounding moderator material is selected such that Neutron radiation from adjacent lanes is detected.

In embodiments where Gamma detectors are shared, further consideration is required to address implications of missing shielding. Due to the absence of shielding for detector assemblies between adjacent traffic ways, the radiation detector assemblies between traffic ways are essentially equally exposed to background radiation effects and vehicle shielding effects of the background radiation from the directions of both adjacent traffic ways (i.e., from the back as well as the front of such detector assemblies). To overcome these effects, the adjusted levels of radiation provided in the controller output signals include levels of radiation processed by a natural background radiation rejection processor that applies a natural background rejection (NBR) signal processing technique to the level of radiation to differentiate changes in the level of radiation caused by non-natural radiation sources as compared to changes in the level of radiation caused by naturally occurring radiation (Naturally Occurring Radioactive Material or NORM) and by vehicle shielding. Use of the NBR technique allows the unshielded radiation detector assemblies positioned between adjacent traffic ways to provide accurate detection of artificial Gamma radiation sources traveling in vehicles within those traffic ways.

The system of the invention preferably includes a set of M traffic sensors respectively coupled to the set of M controllers. Each traffic sensor is associated with a respective traffic way and is operable to produce a traffic signal when that traffic sensor detects a vehicle or other item traveling in the traffic way. Examples of traffic sensors are motion detectors, speed sensors, inductive loops, infrared sensors or light beams, and the like. The controllers are operable to receive and process the traffic signals associated with their respectively coupled traffic sensors in conjunction with any radiation signals received by that controller from respectively coupled radiation detector assemblies to identify which traffic way contains a vehicle transporting a radiation source.

Each radiation detector assembly positioned between adjacent traffic ways comprises at least one radiation detector, such as plastic scintillator material coupled to a photomultiplier, operable to detect levels of radiation, including radiation from a radiation source within a traffic way on either side of the radiation detector. The radiation detectors may be Gamma radiation detectors, Neutron radiation detectors, or both. Other types of detectors can be included as well, such as x-ray detectors.

The Gamma radiation detector assemblies also include at least one amplifier module coupled to the photomultiplier that is operable to receive the detected level of radiation as an electrical signal from the photomultiplier and to process the detected level of radiation to produce the radiation signals and transfer them to the controllers coupled to that radiation detector assembly positioned between adjacent traffic ways. Embodiments include variations such as a single shared detector photomultiplier that provides detector levels of radiation to two separately operating preamplifiers. Alternatively, other embodiments can include separate radiation detector photomultipliers with a single shared preamplifier.

In a preferred configuration, the set of (M+1) radiation detector assemblies are disposed in a substantially planar manner with respect to each other to define a radiation detector plane substantially perpendicular to the M traffic ways.

In certain embodiments of the invention, the data from the Gamma and Neutron radiation detectors linked to a common controller can be correlated on the level of the individual controller in order to have extra sensitivity or less statistical false alarms in respect to the detection of Plutonium isotopes, which emit both Neutron and artificial Gamma radiation.

In one embodiment, if probability P1 is the probability of a setting of a certain alarm threshold for the gamma detector in a false alarm condition, and probability P2 is a probability of a setting of a certain alarm threshold for the neutron detector resulting in a false alarm, embodiments of the invention can use the correlated (i.e., substantially simultaneous) event of an excess of BOTH detectors above their respective alarm thresholds P1 and P2 in order to achieve a significantly reduced false alarm probability P1*P2. In this manner, in order to have acceptable low total false alarm probabilities, the system of the invention can set significantly lower alarm thresholds for the correlated alarm compared to the gamma or neutron only alarm.

BRIEF DESCRIPTION OF THE DRAWINGS

The foregoing and other objects, features and advantages of the invention will be apparent from the following more particular description of embodiments of the invention, as illustrated in the accompanying drawings and figures in which like reference characters refer to the same parts throughout the different views. The drawings are not necessarily to scale, with emphasis instead being placed upon illustrating the embodiments, principles and concepts of the invention.

DETAILED DESCRIPTION

Embodiments of the invention provide a radiation detection system capable of detecting a radiation source within traffic ways. As an example, consider a two-lane highway. A radiation detection system of the invention can detect radiation sources being transported by vehicles traveling in either lane of the highway by providing a first radiation detector, a second radiation detector and a third radiation detector. The first radiation detector and second radiation detector define or border the first traffic way or lane, while the second radiation detector and third radiation detector define or border the second traffic way or lane. The system also includes a first controller that is coupled to the first radiation detector and that is also coupled to the second radiation detector. The first controller is operable to identify a radiation source within the first traffic way when either one or both of the first radiation detector and/or the second radiation detector detect the radiation source passing through the first traffic way in a vehicle. A second controller is coupled to the second radiation detector and is also coupled to the third radiation detector. The second controller is operable to identify a radiation source within the second traffic way when either one or both of the second radiation detector and/or the third radiation detector detect the radiation source passing through the second traffic way. In this manner, embodiments of the invention can share the second detector for detecting radiation sources in both the first and second traffic ways, thus eliminating a requirement for installation and operation of two detectors for detecting the same type of radiation between adjacent traffic ways. Embodiments of the invention save costs, installation time, utilize less real estate, and consume less power that conventional system designs. Since both controllers couple to the middle or second detector, redundancy is provided by the design of the system in the event of failure of one controller.

Unless otherwise stated, "radiation source" as used herein generally indicates a localized artificial or man-made radiation source, as distinguished from natural radiation or background radiation that is generally present at low, but possibly varying, levels. In addition, references to radiation sources that are "in" a vehicle are to be understood to also include sources that are positioned or mounted on the outside of a vehicle.

Figure 1:
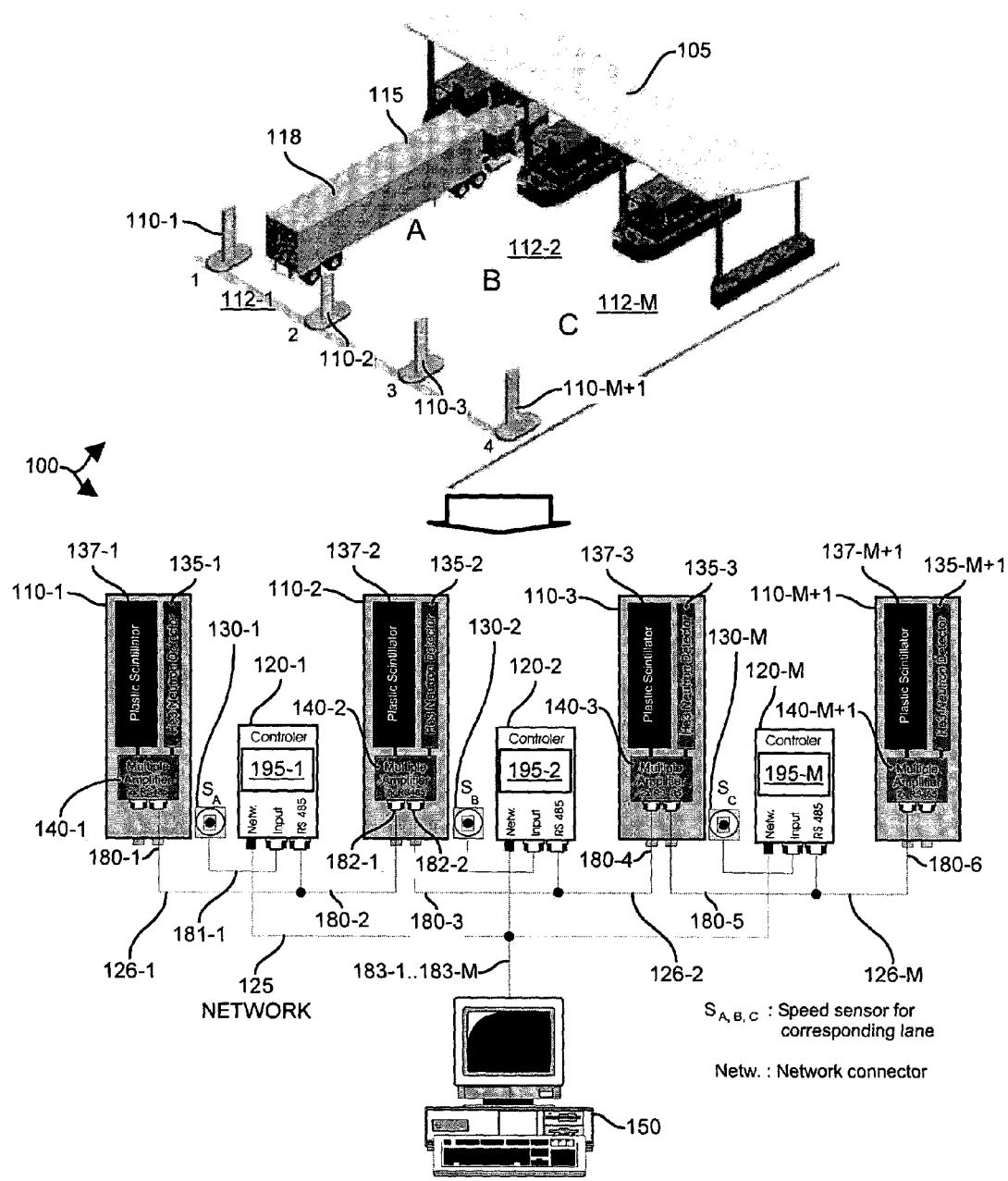
FIG. 1 illustrates a configuration of a radiation detection system in accordance with one embodiment of the invention.

FIG. 1 illustrates an example of a radiation detection system 100 configured in accordance with one embodiment of the invention. The top portion of FIG. 1 is a perspective view of the radiation detection system 100 in use in an example highway installation, while the bottom portion of FIG. 1 illustrates the interconnected components of the radiation detection system 100 in an architectural arrangement or layout. Referring to the upper portion of FIG. 1, the radiation detection system 100 is capable of detecting a radiation source 118 within traffic 115, such as a truck in this example, that can travel within M adjacent traffic ways 112-1 through 112-M, where M is an integer value equal to or greater than two (M is 3 in the embodiment shown in FIG. 1).

The radiation detection system 100 includes a set of (M+1) (i.e., 4 in this example) radiation detector assemblies 110-1 through 110-(M+1). Individual radiation detector assemblies are respectively positioned at each of two sides of each of the M adjacent traffic ways 112. Each radiation detector assembly that is positioned between adjacent traffic ways (e.g., 110-2 between traffic ways 112-1 and 112-2, and 110-3 between traffic ways 112-2 and 112-3) is operable to detect radiation from a radiation source 118 in either of the two adjacent traffic ways 112 adjoining that radiation detector assembly 110. In the illustrated configuration, the set of (M+1) radiation detector assemblies are disposed in a substantially planar or in-line manner with respect to each other to define a radiation detector plane that is substantially perpendicular to the M adjacent traffic ways 112, such that vehicles 115 traveling on the traffic ways 112 must pass through the radiation detector plane formed by the radiation detector assemblies 110.

As an example, if the traffic 115 (i.e., the truck in this example) containing the radiation source 118 travels within one of the traffic ways 112-1 or 112-2, and while traveling in one of those traffic ways, the radiation source 118 is disposed on a side of the vehicle traffic 115 that is proportionately closer to the radiation detector assembly 110-2, then that single radiation detector assembly 110-2 disposed between the traffic ways 112-1 and 112-2 is capable of detecting the radiation source 118 within the vehicle 115. When one of the radiation detector assemblies 110 performs detection of a radiation source 118 within traffic 115, the radiation detection system 100 may in certain situations be able to identify the particular traffic way 112 that contains the vehicle 115 transporting the radiation source 118 and to then notify an appropriate operator within one of the operator booths 105, or at some other location, to take appropriate action to investigate the contents of the identified vehicle 115.

Directing attention to the lower portion of FIG. 1, the radiation detection system 100 configured according to this embodiment of the invention includes a set of M (three in this example in FIG. 1) controllers 120-1 through 120-M. Each controller 120 is associated with a respective traffic way of the M adjacent traffic ways 112. Each controller 120 can be, for example, a computerized device or other electronic or signal processing instrumentation and is coupled to the respective individual radiation detector assemblies 110 positioned at the two sides of the traffic way 112 to which that controller 120 is associated. Accordingly, two controllers 120 (e.g., 120-1 and 120-2, or 120-2 and 120-3) associated with two adjacent traffic ways 112 (e.g., 112-1 and 112-2, or 112-2 and 112-3) each couple to the individual radiation detector assembly 110 (e.g., 110-2 or 110-3) positioned between those two adjacent traffic ways 112. Generally, the controllers 120 are operable to receive radiation signals 180 produced from the radiation detector assemblies 110 coupled to that controller 120 and to identify a radiation source 118 present in either (or to identify sources present in both) of the traffic ways 112 adjacent to that radiation detector assembly 110.

Also shown in FIG. 1 is a set of M traffic sensors 130-1 through 130-M. Each set respectively couples to a corresponding controller 120 in the set of M controllers. Each traffic sensor 130 is thus associated with a respective traffic way or lane 112 and is operable to produce a traffic signal 181 when that traffic sensor 130 detects the presence of a vehicle 115 traveling in the traffic way 112 to which that traffic sensor 130 is associated. The traffic sensors 130 allow the radiation detection system 100 of the present invention to be able to detect when a vehicle is traveling in between a respective pair of radiation detector assemblies 110 in order to help identify which traffic way 112-1 through 112-M contains a vehicle transporting a detected radiation source 118, as will be explained. Each controller 120 is operable to receive and process the traffic signals 181 associated with its respectively coupled traffic sensors 130 in conjunction with any radiation signals 180 received by that controller 120 from respectively coupled radiation detector assemblies 110 to identify which traffic way 112 contains a vehicle 115 transporting the radiation source 118. The traffic sensors 130 can be, for example, motion detectors, speed sensors, infrared sensors, light beams (i.e., that a vehicle 115 intersects), or the like.

As indicated in the top portion of FIG. 1, if the vehicle 115 contains the radiation source 118 on the right hand side (e.g., when the vehicle is viewed from the rear) of the vehicle 115, the radiation detector assembly 110-2 may be activated when the radiation source 118 passes within proximity to this radiation detector assembly 110-2. The radiation detector assembly 110-2 will produce radiation signals 180-2 and 180-3 that are each transmitted over the communications couplings 126 to the respective controllers 120-1 and 120-2. Concurrently with this operation, the traffic sensor 130-1 associated with the traffic way 112-1 will detect the presence of the vehicle 115 between the radiation detector assemblies 110-1 and 110-2. Since there is no traffic or vehicle currently passing in between the radiation detector assemblies 110-2 and 110-3, the traffic sensor 130-2 will not produce a traffic signal 181. As a result, even though the controller 120-2 associated with the traffic way 112-2 is receiving a radiation signal 180-3, since the traffic sensor 130-2 is not indicating that a vehicle is present in the traffic way 112-2, the system 100 determines that the radiation signal 180-3 is not associated with a vehicle and that the signal 180-2 is associated with a vehicle in the lane 112-1.

Embodiments of the invention provide a high level of redundancy and fault tolerance in the event of a failure of a component. In particular, the controllers 120 operate independently of each other such that if one controller 120 (e.g., 120-2) experiences a failure, in certain embodiments at least one non-failed controller 120 (e.g., 120-1 and 120-M in FIG. 1) associated with at least one traffic way 112-1 and 112-M adjacent to the traffic way 112-2 associated with the failed controller 120-2 is operable to receive radiation signal(s) 180 (180-2 and 180-5 in the example in FIG. 1) produced from the individual radiation detector assemblies 110-2 and 110-3 coupled to both the non-failed controller(s) 120-1 and 120-M and the failed controller 120-2. Adjacent controllers 120 can also couple to the traffic sensors 130 in adjacent lanes as well (not shown). In this manner, failure of the controller 120 in one lane can still allow the radiation detection system 100 to function properly and traffic passing within the traffic way 112-2 in the example in FIG. 1 does not have to be rerouted to alternate traffic ways. Stated differently, in one configuration, since the radiation detector assemblies 110 and traffic sensors 130 in "center" lanes (i.e., lanes that have neighboring lanes on both sides) are redundantly coupled to the controllers 120 of each of those neighboring lanes, in the event of a controller failure of a "center" lane, the neighboring non-failed controllers on either side of the failed controller can operate to receive the detector and traffic sensors signals in order to fulfill the objective of detecting a radiation source in the lane associated with the failed controller, and thus traffic in this lane can continue.

Each controller 120-1 through 120-M is operable to produce a controller output signal 183-1 through 183-M indicative of radiation detected by each radiation detector assembly coupled to that controller. The controller output signals 183 can contain a variety of information such as the detected radiation levels of each detector, the identities of the detectors that detected those levels, the controller identity (and hence the traffic way identity), the traffic sensor data such as speed and/or existence of the vehicle during the time of the reading of radiation by the detectors and so forth.

A central computer system 150 is in communication with the set of M controllers 120. A network 125 couples each controller 120 to the central computer system 150. The network 125 may be any type of physical or wireless network that provides suitable high-speed data transmission capability. In one embodiment, the central computer system 150 receives and processes the controller output signals 183 from each controller 120 over the network 125 to determine in which traffic way 112 a radiation source 118 is present. Accordingly, the central computer system 150 can receive all data from all controllers 120 and can cross-correlate data in order to make more accurate identifications of a traffic way 112 in which a vehicle 115 is transporting a radiation source 118. This can include receiving alarm information from multiple controllers and filtering this information to determine weaker alarms and stronger alarms to more accurately identify which traffic way 112 contains the radiation source.

Each radiation detector assembly 110 positioned between adjacent traffic ways 112 comprises one or more radiation detectors 135, 137 that are operable to detect radiation from transported radiation source(s) 118 in the traffic ways 112 on either side of the radiation detector (i.e., from either adjacent lane in the illustrated example). The example radiation detector assemblies 110 in FIG. 1 include two different radiation detectors. Those skilled in the art will understand that any number and type of radiation detectors may exist within the radiation detector assemblies 110. The illustrated example includes a first radiation detector 135 that may be, for example an He3 Neutron radiation detector and a second radiation detector 137 that may be, for example, a Gamma radiation detector constructed of a plastic scintillator material.

Embodiments of the invention provide an amplifier module 140 coupled to the radiation detector(s) 135 and 137 within the radiation detector assemblies 110. The amplifier module 140 is operable to receive the detected radiation as one or more electrical signals from the radiation detectors 135 and 137. The amplifier module 140 can process the detected radiation to produce the radiation signal(s) 180 for transfer from the radiation detector assembly 110 to the controllers 120 coupled to that radiation detector assembly 110 positioned between adjacent traffic ways 112. The transfer of information from the amplifier modules 140 to the controllers 120 can take place over a physical or a wireless communications channel.

The amplifier modules 140 can include a shared preamplifier in one configuration or alternatively, can provide separate or dual preamplifiers for each of radiation detector 135 and 137. In the single amplifier configuration, the amplifier module 140 comprises a single shared preamplifier coupled to the first radiation detector 135 and to the second radiation detector 137. A shared preamplifier is operable to receive, as electrical signals, the radiation detected by the first and second radiation detectors 135 and 137. The shared preamplifier (e.g., 140-2) further includes a first radiation signal output interface 182-1 (i.e., only labeled on radiation detector assembly 110-2) and a second radiation output signal interface 182-2 in communication with respective controllers 120-1 and 120-2 associated with the two traffic ways 112-1 and 112-2 adjacent to the radiation detector assembly 110-2 that houses the shared preamplifier 140. The radiation output signal interface associated with the amplifier modules 140 (and preamplifiers) may be, for example, a serial interface such as an RS-485 bus interface.

In the dual amplifier configuration (not shown), the amplifier module 140 comprises a first preamplifier and a second preamplifier. Each of the two preamplifiers has a radiation signal output interface 182 in communication with one of the controllers 120 associated with each of the two traffic ways 112 adjacent to the radiation detector assembly 110. The preamplifiers are operable to receive the detected radiation from the radiation detector(s) 135 and 137 and to process the detected radiation into respective radiation signals 180 for transfer to the respective controllers 120 with which those preamplifiers are in communication.

According to some embodiments of the invention, the radiation detector assemblies 110 positioned between adjacent traffic ways 112 include unshielded radiation detectors, such as the Gamma radiation detectors 137. Since the detectors are unshielded, they are exposed to background radiation and vehicle shielding effects from both adjacent traffic ways 112 on either side of that radiation detector assembly 110.

In particular, background radiation in the form of ambient Gamma rays that are present in the atmosphere impacts the unshielded Gamma radiation detector 137, thus resulting in higher levels of detected background Gamma radiation (as opposed to shielded detectors used in conventional systems of type A. In addition, since the Gamma radiation detectors 137 are unshielded, when a vehicle 115 such as the large truck 115 illustrated in FIG. 1 passes by the unshielded radiation detector 137 within the radiation detector assembly 110, the vehicle 115 itself (i.e., the large body of the truck and trailer) provides a shielding effect that lowers the overall exposure or dosage of background radiation incident upon the unshielded radiation detector 137. The amount of the vehicle shielding effect (i.e., vehicle shielding dosimetry) varies depending upon the physical configuration of the vehicle (e.g., size, shape, construction material), as well as the distance of the vehicle from the detector assembly 110, and may include other factors.

In conventional type A system designs as explained above, shielding is provided to limit the exposure to background radiation in a neighboring lane and to limit the effects of the vehicle shielding change that modifies this background radiation level during vehicle presence (i.e., approach, passing by, and departing away from detector assembly in the neighboring traffic way) in order to provide the ability to accurately detect transported radiation sources 118. Embodiments of the invention have overcome this detector shielding requirement or limitation as required in conventional type A systems and do not require shielding of the Gamma radiation detectors 137. As a result, one single or individual Gamma radiation detector 137 is capable of detecting a radiation source 118 within either of the adjacent traffic ways 112 on either side of that unshielded Gamma radiation detector 137. As a result, s savings are achieved in terms of system costs, system complexity and in installation and materials requirements due to the elimination of shielding and thus the elimination of a requirement for two detector assemblies (i.e., two shielded detectors) in between each adjacent traffic way 112, as is provided by conventional type A systems.

To overcome the effects of the lack of shielding the Gamma radiation detectors 137, components of the radiation detection system 100 can compensate for, or adjust, the levels of radiation detected by the unshielded radiation detectors 137. Such compensation or adjustment can take place, depending upon the embodiment of the invention, either within the radiation detector assemblies 110 (e.g., within preamplifiers 140) or within the controllers 120.

To adjust or compensate detected radiation levels to account for the removal of shielding on the radiation detectors 137 and to compensate for vehicle shielding effects, embodiments of the invention employ a natural background radiation rejection processor 195 operable in conjunction with the unshielded Gamma radiation detector 137 to receive radiation signals from the radiation detector 137. The radiation signals include information representative of Gamma radiation incident on the unshielded Gamma radiation detector 137. The natural background radiation rejection processor 195 can apply a natural background rejection signal processing technique to the radiation signals to differentiate between changes in radiation caused by artificial or non-natural radiation sources 118 and changes in the radiation caused by naturally occurring radiation material (NORM) sources. In particular, the natural background radiation rejection processor 195 operates according to techniques, mechanisms and circuitry disclosed in issued German Patent No. DE 197 11 124 C2, the entire disclosure and teachings of which are hereby incorporated by reference. As used herein, the teachings of this issued German Patent are referred to as Natural Background Rejection (NBR).

As an example of the use of the NBR processing technique in accordance with embodiments of the invention, each controller 120 can be configured with a natural background radiation rejection processor 195. As a result of the functionality of this NBR processor 195, the controller output signals 183 from each controller 120 provide an adjusted level of radiation detected by the radiation detector assemblies 110 coupled to that controller 120. The controller output signals 183 can also contain an identity of the radiation detector assembly 110 associated with the adjusted level of radiation.

The central computer system 150 is operable to receive and correlate the adjusted levels of radiation 183 from a plurality of radiation detector assemblies 110, as will be explained further, to identify patterns of correlated levels of radiation that indicate the existence of a radiation source 118 within a specific traffic way 112 of the M adjacent traffic ways. In this manner, embodiments of the invention are capable of providing single radiation detector assemblies 110 between adjacent lanes that utilize one or more unshielded radiation detectors 137 in conjunction with NBR processing to eliminate or significantly reduce (to an acceptable level) the problematic effects of increased background radiation (due to the removal of shielding) and vehicle shielding effects that result from vehicles providing shielding of the naturally occurring background radiation.

In the example provided, the adjusted levels of radiation provided in the controller output signals 183 include levels of radiation processed by a natural background radiation rejection processor 195 operable either in the controllers 120 or in the radiation detector assemblies 110. The NBR processors 195 apply the natural background rejection signal processing technique explained in the aforementioned reference to German Patent to compensate for the absence of shielding of the radiation detectors of the radiation detector assemblies positioned between adjacent traffic ways.

For implementations that provide the NBR processor 195 that is operable in conjunction with the amplifier module 140 (i.e., in detector assemblies 110), such configurations receive a level of radiation detected by the radiation detector 137 and apply the natural background rejection signal processing technique to the level of radiation to differentiate between changes in the radiation caused by non-natural radiation sources and changes in the radiation caused by naturally occurring radiation sources such that each of the detector assemblies 110 positioned between adjacent traffic ways 112 do not require shielding from background radiation. Further details of this process will be explained later.

Is to be understood hat the aforementioned description of embodiments of the invention in FIG. 1 is not intended to be limiting. Alternative configurations are possible and contemplated within the scope of embodiments of this invention. As an example, using redundant components (e.g. photomultipliers, preamplifiers) can eliminate an impact of a failure within the signal processing chain explained above.

To achieve maximum cost savings, embodiments of the invention can provide sharing of radiation detector assemblies 110. This can include using shared Gamma ray detectors 137 and shared Neutron detectors 135. In an alternative configuration of the invention, the Gamma ray detectors 137 can be duplicated within each radiation detector assembly 110 and shielding can be provided for each from the background radiation and vehicle shielding effects explained above. However, within this radiation detector assembly 110-1 that uses separate Gamma radiation detectors 137, the Neutron detector 135 could be shared for use in detecting Neutron radiation in both traffic ways 112 adjacent to the radiation detector assembly 110. In other words, in an alternative configuration, there are separate Gamma radiation detectors 137 each having a respective shielding while there is a shared Neutron detector.

In a further alternative, due to the relatively high penetration capability of Neutron radiation, the Neutron detectors 135 can be interspersed and disposed between every two radiation detector assemblies 110-1 through 110-(M+1), such that some (e.g., every other or every third) radiation detector assemblies 110 do not contain a Neutron radiation detector 135.

Figure 2:
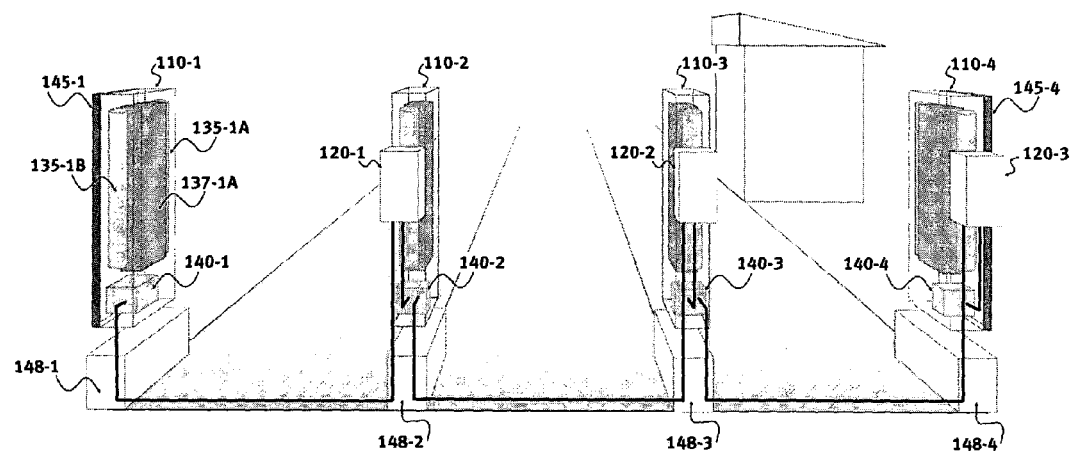
FIG. 2 is a perspective view of a radiation detection system configured in accordance with one embodiment of the invention.

FIG. 2 provides a perspective view of the radiation detection system 100 configured according to one example embodiment of the invention. The reference numerals indicating components of the radiation detection system 100 that have been previously described with respect to FIG. 1 will not be explained further with reference to this figure. One difference, however, between the embodiment illustrated in FIG. 2 and the embodiment illustrated in FIG. 1 is that in FIG. 2 the outermost or edge radiation detector assemblies 110-1 and 110-(M+1) do contain shielding material 145-1 and 145-2 on their respective outermost sides that face away from the traffic ways 112. Accordingly, this example illustration indicates how an existing system configured according to a conventional Type A system design that utilizes shielding can be outfitted or retrofitted with embodiments of the invention by removal of the shielding material from the radiation detector assemblies 110 that exists between adjacent traffic ways 112. Other modifications to the conventional design include, but are not limited to, modifying the controllers 120 with preamplifiers 140 to include natural background rejection processors 195 to compensate for the shielding removed from the radiation detector assemblies in between adjacent traffic ways 112. Controller couplings can be modified as well to allow redundancy in coupling to neighboring traffic sensors and detector assemblies. In addition, each radiation detector assembly 110 is illustrated as containing a foundation 148.

Figure 3:
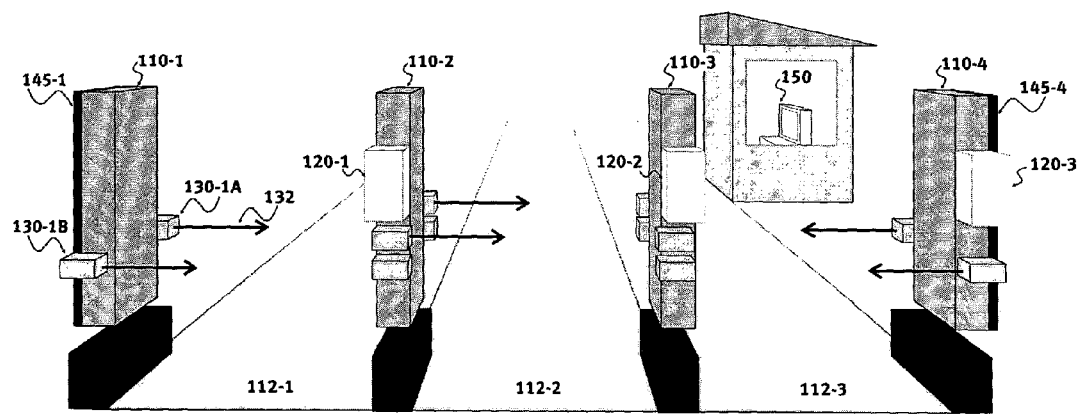
FIG. 3 is a perspective view of a radiation detection system configured in accordance with one embodiment of the invention that shows the use of traffic sensors to detect when a vehicle is in a traffic way.

FIG. 3 provides another illustration of a radiation detection system 100 configured in accordance with one example embodiment of the invention that is similar to the view in FIG. 2. In FIG. 3, however, the radiation detection system 100 illustrates the use of traffic sensors 130 that in this example project light beams 132 across each of the adjacent traffic ways 112. Interruption of the light beams 132 provides a presence signal or traffic signal as a vehicle approaches the radiation detector assemblies 110 and unblocking of the light beams indicates the departure of the vehicle from the vicinity of the detector assemblies 110. In addition, this figure illustrates an operator booth 105 containing the central computer system 150 that can coordinate operation of the controllers 120 and traffic sensors 130 in order to determine which vehicle 115 in which traffic way 112 is transporting a radiation source 118.

Figure 4:
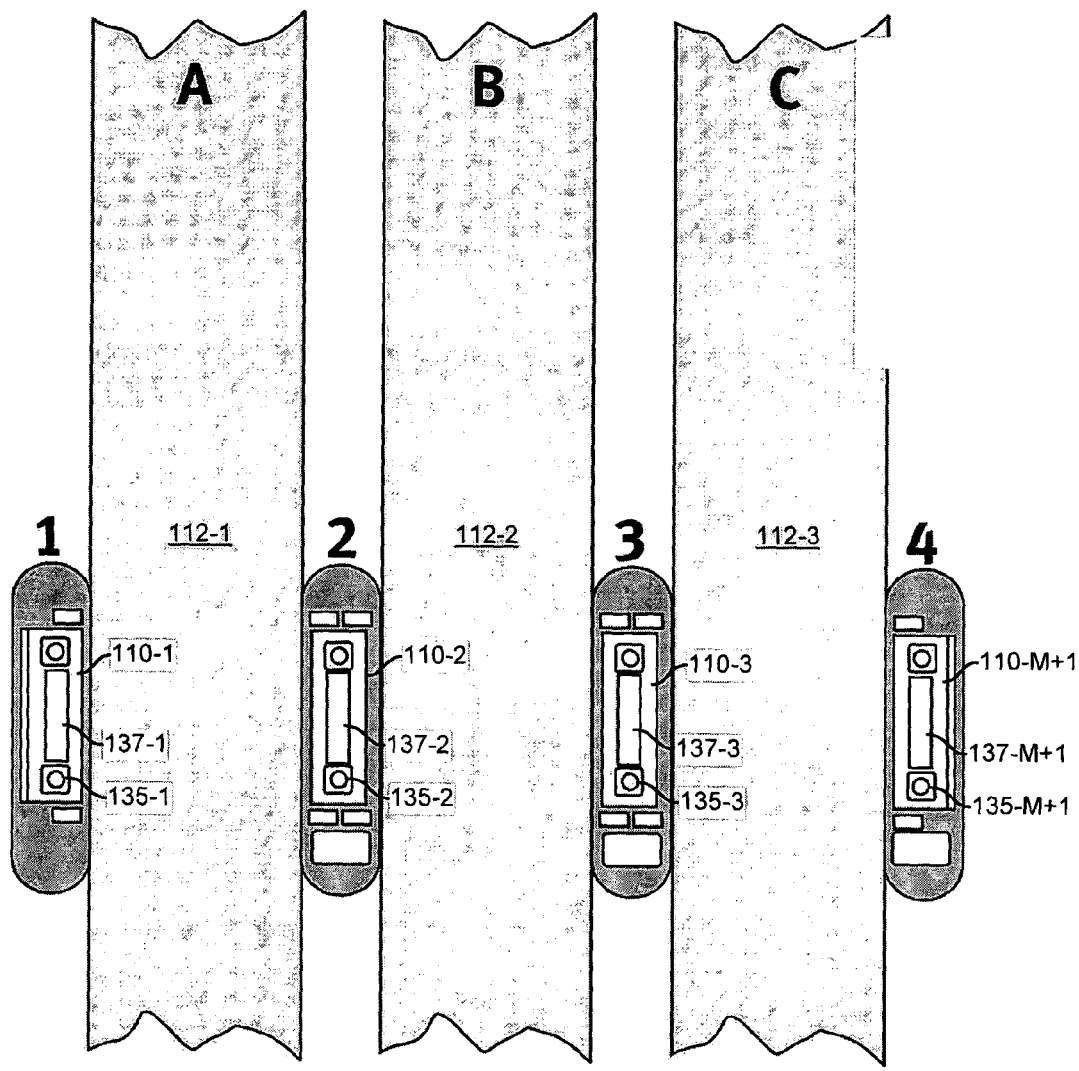
FIG. 4 is a top-down view of a radiation detection system configured in accordance with one embodiment of the invention.

FIG. 4 provides a top-down view of radiation detection system 100 configured in accordance with one example embodiment of the invention. This view of the radiation detection system 100 illustrates how the architecture, design and operation of embodiments of the present invention provide significant savings in the required hardware that needs to be installed between adjacent traffic ways 112. In particular, in this example, each radiation detector assembly 110-2 and 110-3 is only required to have a single shared Gamma radiation detector 137-2 and 137-3 that the system utilizes as explained above to detect radiation sources 118 that may be present within the either of the traffic ways 112 adjacent to those radiation detector assemblies 110-2 and 110-3. Since neither shielding nor a second Gamma radiation detector are required, implementation of a radiation detection system 100 in accordance with embodiments of the invention can be significantly faster, less complicated and less expensive than conventional Type A system designs.

Figure 5A:
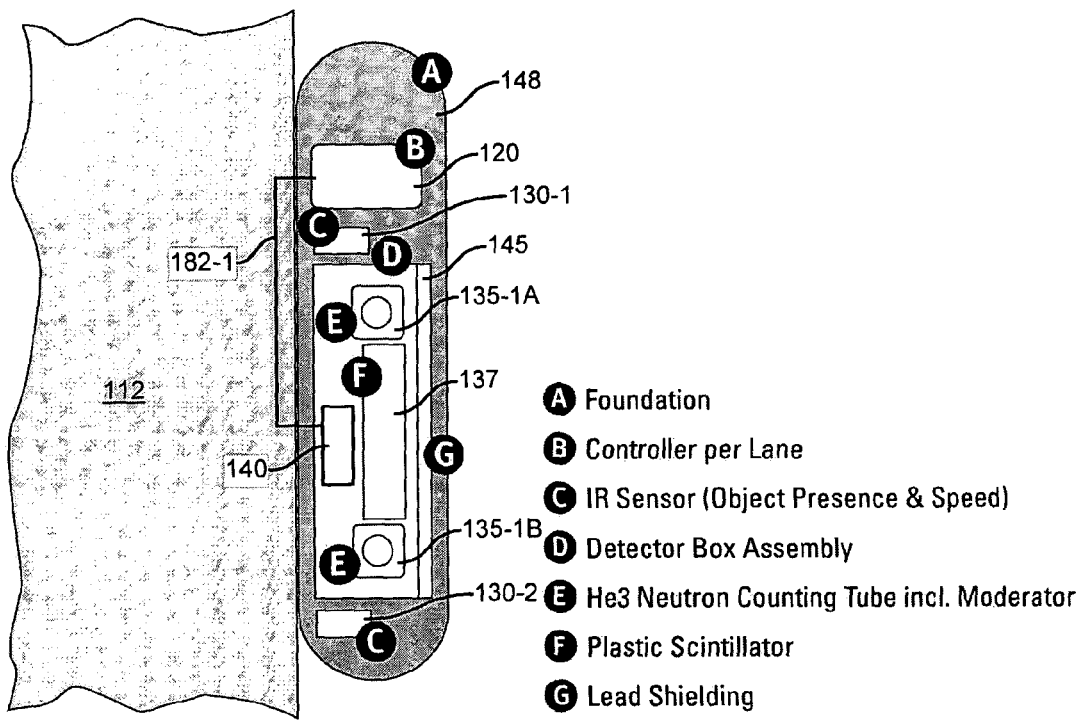
FIG. 5A is a top-down component layout view of a detector installation according to one embodiment of the invention for use adjacent to an outermost traffic way in a multi-traffic way installation.

FIG. 5A illustrates an example of a radiation detector installation 102 that includes the overall combination of a radiation detector assembly 110, a controller 120, traffic sensors 130 and a foundation 148 as used on the outermost traffic ways of a multi-lane traffic way. The foundation 148 may be, for example, a steel housing or other enclosure or a concrete platform that supports the controller 120, traffic sensors 130, and the radiation detector assembly 110. The radiation detector assembly 110 in this example shows the placement of two He3 Neutron detectors 135-1A and 135-1B and one Gamma radiation detector 137. The Gamma radiation detector may be a photomultiplier mounted to a plastic scintillator material that optimally detects Gamma radiation as explained in detail below. This particular example shows the placement of shielding 145 on the outermost side of the radiation detector assembly 110. The shielding 145 can be used for installations of radiation detector assemblies placed on the outermost sides (e.g., far left and far right) of the M adjacent traffic ways. It is to be understood that for installations between adjacent traffic ways, this shielding 145 is removed. It is also to be understood that this shielding 145 is not required, even on the outermost detector assemblies 110, but is shown here for completeness.

This example shows the use of a single amplifier module 140 that couples to each Neutron radiation detector 135-1A, 135-1B, as well as to the Gamma radiation detector 137. The amplifier module 140 includes a first radiation signal output interface 182-1 that couples to the controller 120. Since this example illustrated radiation detector installation 102 configuration is for placement at an outermost side of the M adjacent traffic ways 112 (i.e., is for use on either the far left or far right as illustrated in FIGS. 2 and 3 (i.e., due to the existence of the shielding 145), the second radiation signal output interface 182-2 of the amplifier module 140 is not coupled to another adjacent controller 120 (since there is no adjacent traffic way to the outermost side of the edge traffic ways 112-1 and 112-M). If this installation 102 were used in between adjacent traffic ways 112, the second radiation signal output interface 182-2 would be coupled (e.g., via an RS-485 bus cable or other interface) to a controller 120 associated with the other adjacent traffic way 112.

This configuration may be installed for use within an environment such as a roadside highway installation or other traffic way 112. In this example, the two traffic sensors 130-1 and 130-2 are disposed on opposite sides of the radiation detector assembly 110, but in parallel with the traffic way 112 so that this configuration can be used with traffic moving in either direction on the traffic way 112.

Figure 5B:
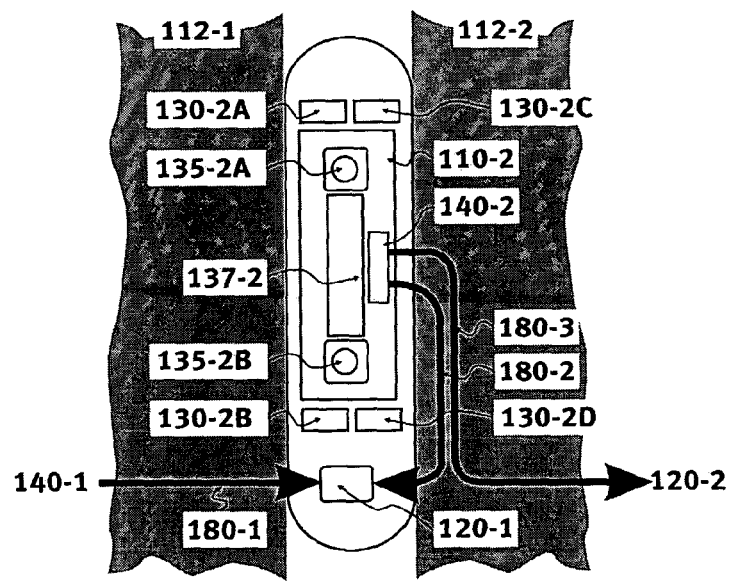
FIG. 5B is a top-down component layout view of an unshielded detector installation according to one embodiment of the invention for use between adjacent traffic ways.

FIG. 5B illustrates an embodiment of the invention that provides a configuration of a radiation detector assembly for use between adjacent traffic ways 112. The configuration in FIG. 5B provides an unshielded shared Gamma detector 137-2 that is capable of detecting a radiation source within either traffic way 112-1 or 112-2. Note that the controller 120-1 is coupled via data communications links 180-1 and 180-3 (through amplifier 140-2) to the neighboring detector assemblies (not shown) on opposite sides of the traffic ways 112-1 and 112-2. This enables the controller 120-1 to receive presence sensor signals and radiation signals from the neighboring detector assemblies in the event that a controller of a neighboring assembly fails. Thus redundancy is provided in the design of embodiments of the invention.

It is to be understood that embodiments of the invention are not limited to applications involving vehicular highway traffic to transport radiation sources 118 within vehicles 115 such as cars and/or trucks. Embodiments of the invention are intended to be applicable to many different types of traffic ways 112 in which any type of vehicle may be capable of transporting a radiation source 118. Examples include railroad installations, walkways or hallways (in which people correspond to the vehicles 115), manufacturing facilities (e.g., conveyor belt systems, assembly lines) and other types of traffic ways 112.

Figure 6:
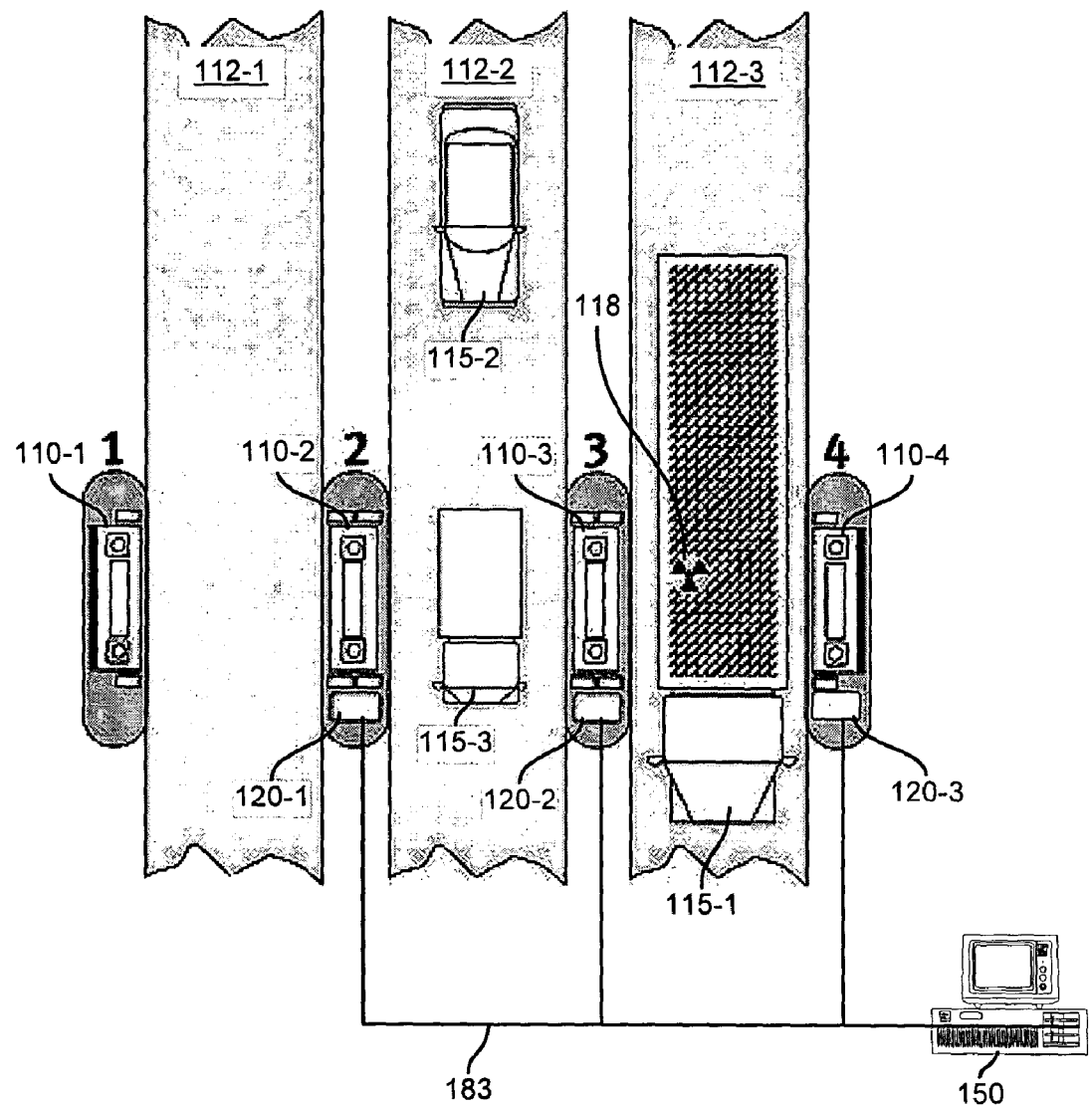
FIG. 6 illustrates a hypothetical traffic scenario in which a vehicle is transporting an artificial (non-natural) radiation source though a radiation detection system configured in accordance with embodiments of the invention.

FIG. 6 illustrates an example of the use of the radiation detection system 100 in an example traffic scenario involving a large vehicle 115-1 transporting a radiation source 118 on a traffic way 112-3 of a three lane highway (i.e., three traffic ways 112-1, 112-2, 112-3), while other vehicle traffic 115-2 and 115-3 is present in the traffic way 112-2. According to this embodiment of the invention, the two radiation detector assemblies 110-2 and 110-3 positioned between adjacent traffic ways include unshielded gamma radiation detectors (e.g., 137) and are thus susceptible to incident background radiation exposure and also to vehicle shielding or limiting effects from the direction of both adjacent traffic ways (i.e., traffic ways 112-1 and 112-2 for detector assembly 110-2, and traffic ways 112-2 and 112-3 for detector assembly 110-3).

A brief explanation of vehicle shielding effects on background radiation will now be provided to assist in further understanding operations of embodiments of the invention.

In FIG. 6, the presence of the small truck 115-3 in between radiation detector assemblies 110-2 and 110-3 creates or induces a vehicle shielding effect on naturally occurring background radiation received by, or incident upon, the unshielded radiation detectors (e.g., the Gamma radiation detectors 137, as shown in previous figures) within those detector assemblies 110-2 and 110-3. The reason for this is that the material from which the small truck 115-3 is constructed and its contents can interfere with, and provide some shielding from, this naturally occurring background radiation. This vehicle shielding effect is also present to a somewhat greater extent due to the presence and size of the large truck 115-1 in between radiation detector assemblies 110-3 and 110-4. In particular, the radiation detector assembly 110-3 is effectively shielded from the both directions of the adjacent traffic ways 112-2 and 112-3 due to vehicles 115-1 and 115-3. This vehicle shielding exists to a somewhat larger extent from the larger truck 115-1 as opposed to a somewhat lesser shielding effect induced by the smaller truck 115-3. The actual amount of the vehicle shielding effect on naturally occurring background radiation depends on various factors such as the size and shape of the vehicle 115, the material from which the vehicle 115 is constructed, the distance of the vehicle 115 from the radiation detector assemblies 110 and possibly other factors.

Since the Gamma radiation detectors 137 within the detector assemblies 110-2 and 110-3 are unshielded, when no vehicle traffic is adjacent to either side of such detector assemblies, the unshielded Gamma radiation detectors 137 detect the highest rating or dosage of background radiation incident upon those unshielded detectors 137. However, as the vehicles 115 approach and become positioned adjacent to those detector assemblies, the shielding effects of those vehicles 115 lowers the incident dosage of background radiation received and detected by those unshielded detectors 137. Concurrent with this vehicle shielding effect phenomenon, the increased radiation produced by the radiation source 118 in the vehicle 115-1 that falls incident upon the unshielded radiation detectors 137 offsets or counters the shielding effect induced by the presence of the vehicle 115 itself. In other words, while the presence of one or more vehicles 115 induces an effect that lowers the overall radiation detected by the unshielded radiation detectors 137, the existence or presence of a radiation source 118 within one of the vehicles operates to counteract this shielding effect.

As noted above, conventional radiation detection systems include shielding on all detector assemblies positioned between adjacent traffic ways. The shielding provided in such conventional system designs is required to avoid background radiation count rate decreases induced by vehicles passing the detector assembly at its backside (i.e., in a traffic way adjacent to the shielded detector, but for which that detector is not responsible for monitoring). In conventional designs that use the shielding, the natural background is thus continuously maintained at reduced levels and remains less affected when a vehicle passes in an adjacent traffic way. This is because the lead shield already shields the natural background radiation to some extent and that the remaining portion of background radiation is further shielded by the vehicle in such conventional Type A systems.

Due to the fact that the natural Gamma background radiation includes a significant portion of very high energy Gamma rays, very thick shielding of the order of 10 cm lead would be required to fully suppress the effect of the backside traffic. Weight and cost of such lead shielding typically restricts the de facto mounted shielding to less than about 1 cm, so there is still significant inter-lane crosstalking of the background radiation shielding effects caused by passing vehicles.

However, embodiments of the invention have significantly overcome such difficulties based in part on an observation that by utilizing a natural background rejection signal processing technique in conjunction with unshielded radiation detectors, the system of the invention can overcome the uncertainty and ambiguity caused by vehicle shielding effects which are then offset by increased radiation from an artificial radiation source 118 transported in a vehicle 115 adjacent to the detector assemblies 110.

In particular, the traffic scenario illustrated in FIG. 6 represents one example of a difficult or worst-case radiation source detection scenario since two traffic ways 112-2 and 112-3 each contain vehicles 115-1 and 115-3, one of which is transporting an artificial radiation source 118 and the other of which is not. Suppose for this example that the radiation source 118 is an emitter of Gamma radiation. Embodiments of the invention can employ the natural background rejection technique to still trigger an alarm due to an artificial radiation source 118 whereas a conventional Type B system without shielding cannot perform this task.

Figure 7:
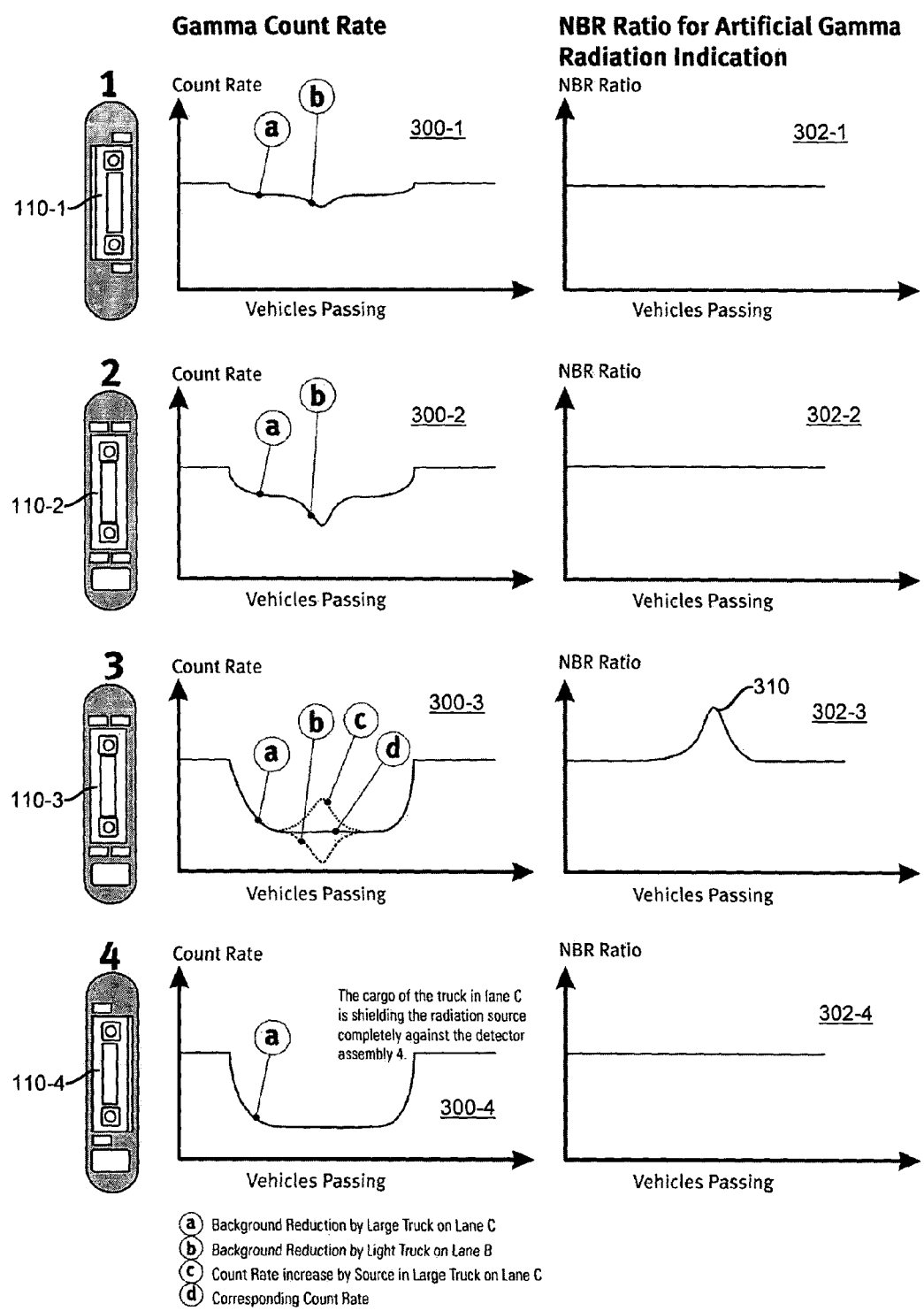
FIG. 7 illustrates timewise plots representative of detected Gamma radiation levels and the application of a natural background rejection technique during operation of detector assemblies in the hypothetical traffic scenario in FIG. 6.

FIG. 7 provides two columns of graphs 300, 302 that represent radiation measurement and analysis data produced according to operations of embodiments of the invention based on the example traffic scenario illustrated in FIG. 6 and explained above. In FIG. 7, each of the four rows of graphs 300 and 302 represent radiation measurement and processing data associated with the corresponding radiation detector assemblies 110-1 through 110-4 shown to the left of those graphs in each row. The first column of graphs 300-1 through 300-4 represents the Gamma count rate or measurement of Gamma radiation detected (versus time) by each of the radiation detector assemblies 110-1 through 110-4 for the example traffic scenario illustrated in FIG. 6. The second column of graphs 302-1 through 302-4 represents data produced according to embodiments of the invention by processing the Gamma count rate data of the graphs 300 according to the natural background radiation rejection (NBR) processing technique employed within the natural background rejection processor 195 configured within embodiments of the invention.

In particular, referring to the first column of graphs 300 that represent the Gamma count rates detected by the respective radiation detector assemblies 110-1 through 110-4, the flat line portions of the Gamma count rate graphs at the beginning and ending of each graph 300 for each radiation detector assembly 110 represent measured or detected levels of natural background radiation when no vehicles 115 are passing between any other radiation detector assemblies 110. In contrast to the flat line portions of the Gamma count rate graphs 300, the areas of these graphs labeled by the lowercase "a" in a circle indicate the amount of the vehicle shielding or vehicle background reduction experienced by each radiation detector assembly 110 due to the effects of vehicle background shielding produced by the presence of the large truck vehicle 115-1 within the third traffic way 112-3 in the example traffic scenario illustrated in FIG. 6.

Notice that for the radiation detector assemblies 110-3 and 110-4, the areas of the Gamma count rate graphs 300 labeled with the lowercase "a" are significantly reduced due to the large shielding effects of the large truck 115-1 positioned relatively close to each of these radiation detector assemblies 110-3 and 110-4. Also notice that the shielding effects of the large truck 115-1 are also experienced, though to a somewhat lesser extent, by each of the other radiation detector assemblies 110-1 and 110-2 as shown by their respective graphs 300-1 and 300-2. Accordingly, as a result of vehicle shielding from a vehicle 115 such as a large truck, each radiation detector assembly 110 in the entire radiation detection system 100 for this three-lane arrangement configured in accordance with embodiments of the invention experiences some vehicle shielding effects, so as to reduce the level of detected natural background radiation.

Directing attention now to the portions of the first three Gamma count rate graphs 300-1, 300-2 and 300-3 labeled with a lowercase "b" in a circle, the "b" areas of these graphs represent background radiation reduction experienced by the radiation detector assemblies 110-1 through 110-3 due to the presence of a small truck 115-3 in the middle traffic way 112-2 in FIG. 6. As is apparent, the light truck 115-3 serves to further reduce the amount of naturally occurring background radiation detected by the three radiation detector assemblies 110-1 through 110-3. For these three detector assemblies 110-1, 110-2 and 110-3, the combined effects of vehicle shielding from both the large truck 115-1 and a small truck 115-3 have a compounding effect that further reduces exposure to background radiation for these detector assemblies. Note that due to the size of the large truck 115-1, the radiation detector assembly 110-4 does not experience substantial vehicle shielding from the small truck 115-3.

Directing attention now to Gamma count rate graph 300-3 produced from radiation measured by the radiation detector assembly 110-3, and specifically to the graph area labeled with the lowercase "c" in a circle, this "c" graph area represents the count rate increase by the radiation source 118 existing within the large truck 115-1 in the traffic way 112-3, as experienced by the unshielded Gamma radiation detector 137 within the radiation detector assembly 110-3. Note that areas of the graph 300-3 labeled "b" and "c" tend to cancel each other out to provide a resulting or corresponding Gamma radiation measurement or count rate labeled with the lowercase "d" in this example.

Directing attention to the second column of graphs 302-1 through 302-4, the natural background radiation rejection processor(s) 195 operating either within the amplifier modules 140 or within the controllers 120 apply a natural background rejection signal processing (i.e., NBR) technique to the radiation signals measured in the corresponding graphs 300-1 through 300-4 to differentiate changes in levels of radiation caused by non-natural radiation sources such as source 118 as compared to changes in levels of radiation (e.g., locations "a" and "b") caused by naturally occurring radiation sources such as background radiation. In other words, the natural background rejection (NBR) signal processing technique is unaffected by the vehicle shielding issue, and the natural background radiation ratio for the artificial Gamma radiation 118 remains stable within each of the radiation detector assemblies 110-1 through 110-4 and only registers for the radiation detector assembly 110-3 (since the artificial radiation source 118 passes closest to this detector assembly 110-3).

Since the radiation detector assembly 110-3 is connected to both controllers 120-2 and 120-3, and vehicles were simultaneously present in both traffic lanes (112-2 and 112-3) associated with these controllers (in this particular example), in some instances the system 100 may not be able to unambiguously determine in which of these lanes 112-2 or 112-3 the radiation source 118 is present, and both the large truck 115-1 and the small truck 115-3 would need to be either stopped or retested as they re-pass separately (non-simultaneously) through traffic way(s). Importantly, however, application of the NBR technique overcomes the effects that truck shielding might otherwise have had in preventing detection of the radiation source 118.

The natural background radiation rejection processor 195 operable either in the controllers 120 or in the radiation detector assemblies 110 applies the natural background rejection (NBR) signal processing technique that implements a radiation counting system that overcomes the limitations of conventional gross and spectroscopy methods for counting or measuring radiation levels. NBR also provides a counting technique that avoids high cost and complicated calibration while facilitating a simplistic setup process. Specific features of the NBR counting system implemented in embodiments of the invention within the natural background radiation rejection processor 195 include:

Automatic compensation to fluctuations in natural background conditions;
Discernment between natural (e.g. fertilizer, bricks, etc.) and artificial radioactive sources;
NBR is not inhibited by shielded sources which smear the spectrum; and
Facilitation of alarm thresholds lower than the background count rate.

The NBR system operates in embodiments of the invention by utilizing plastic scintillators (e.g., of polyvinyltoluene or polystyrene) as the Gamma radiation detectors 137. Such plastic scintillators offer the benefits of a large detection area and relative high efficiency but supply somewhat less energy resolution when compared to NaI and Germanium detector types. They do however, provide sufficient energy information to adequately distinguish between background, (Naturally Occurring Radioactive Material (NORM), and artificial or man-made materials 118 and are sufficient for use in embodiments of this invention.

One operating principle of the NBR technique utilizes the fact that the Gamma interaction with the organic plastic scintillator material in the radiation detectors 137 is almost entirely through Compton Scattering. The low atomic number of the elements in the plastic scintillation material within the radiation detectors 137, in conjunction with the relatively low density of 1.035 $g/cm^3$, results in a higher percentage of gamma rays that experience a partial energy loss only. The remaining and varying portion of the energy collected by the plastic scintillator results in a lower energy scattered across the Compton Continuum. Other than the Compton Edge, where the energy spectrum resulting from the scattered energies suddenly drops off, no clean or consistently identifiable shape or photo peak is manifested. This normally undesirable effect, which is an inherent part of the plastic scintillator radiation detector 137 that are suitable for use in embodiments of the invention, becomes a key component in the NBR counting technique.

The natural background radiation rejection processor 195 operates in embodiment of the invention to detect disruptions of the normal energy distribution characterizing normal background conditions as perceived by the plastic scintillator radiation detectors 137.

Figure 8:
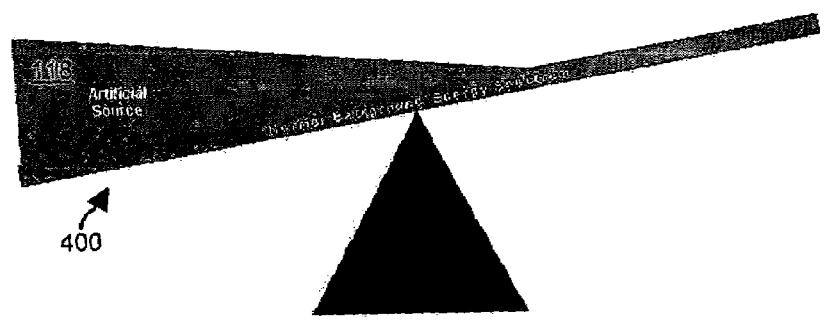
FIG. 8 illustrates an example of background radiation equilibrium unbalance.

As shown in FIG. 8, anytime an artificial radiation source 118 manifests itself such as in a vehicle 115, the background equilibrium of exposure experienced by the radiation detector assemblies 110 becomes unbalanced as shown at location 400, tipping to one side or the other depending upon the nature of the source(s) 118. In most cases, however, the balanced is tipped towards the lower energy side due to Compton Scattering as noted above. This loss from the normal equilibrium state results in a deviation, which is both detectable and measurable by the NBR technique within embodiments of this invention.

Figure 9:
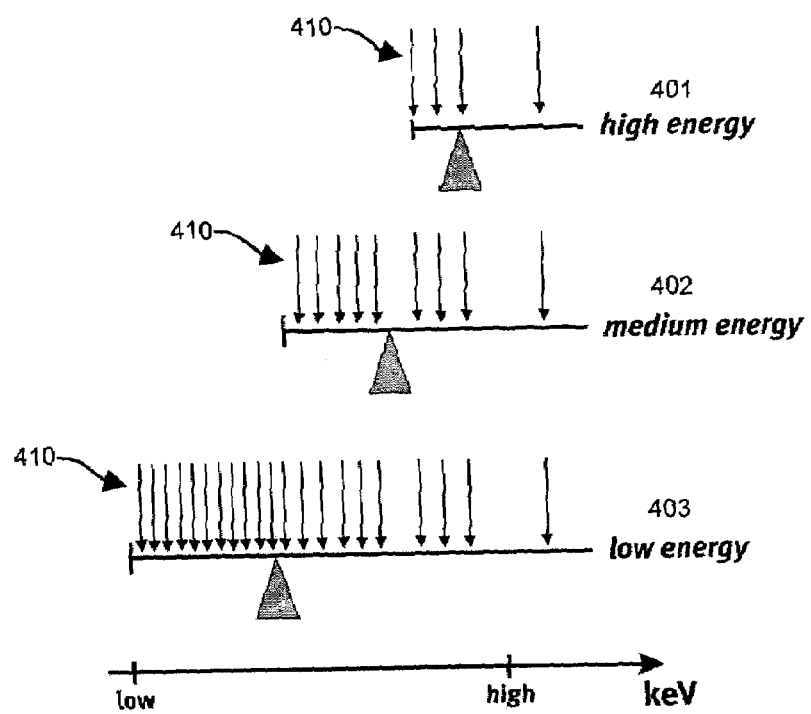
FIG. 9 illustrates how the NBR technique utilized by this invention divides the background radiation energies into separate channels that can be counted individually.

FIG. 9 illustrates how the NBR processor 195 can measure the normal background distribution in one embodiment by dividing the Gamma energy spectrum into several (e.g., three in this example) discrete counting channels. The discrete counting channels include three energy windows, covering the lower energy 401, middle or medium energy 402 and higher energies 403 as illustrated. The NBR process 195 can monitor radiation counts of background radiation 410 on each of the individual channels 401 through 403 (three channels used as an example only) to provide real-time processing, measurement and a corresponding alarm in the event of an unexpected radiation source 118. By observing the existing background energies 410 (in the absence of any artificial sources), the NBR system processor 195 ascertains the balance of energies in their equilibrium state. The self-adjusting algorithms that the processor 195 employs automatically "learn" and remember the equilibrium state for subsequent comparison purposes in the measurement cycle.

Given that background conditions change, the NBR processor 195 can also accommodate fluctuating intensity of background influences which do not affect the overall equilibrium but rather exert either more or less pressure across the balance within prescribed limits. The NBR processing technique used herein separately factors in Cosmic influences for each specific detector 137 to additionally accommodate the overall altitude above sea level and the orientation of the detector with respect to the ground.

FIG. 9 illustrates background radiation in an equilibrium state as measured by the NBR processor 195 of this invention when the background radiation is presently not under the influence of vehicle shielding (i.e., no vehicles are passing). To measure the disruption to this balanced state by man-made or artificial sources, the NBR technique in this example performs three ratio analyses utilizing the energy measurement channels 401 through 403. These three ratio channels or energy levels 401, 402 and 403 are referred to herein as the NBR channels. Anytime any one of these NBR ratios fall outside of a prescribed limit, which may be adjusted by the administrator, the NBR system annunciates an alarm condition identifying the specific alarm type for a specific traffic way 112.

Figure 10:
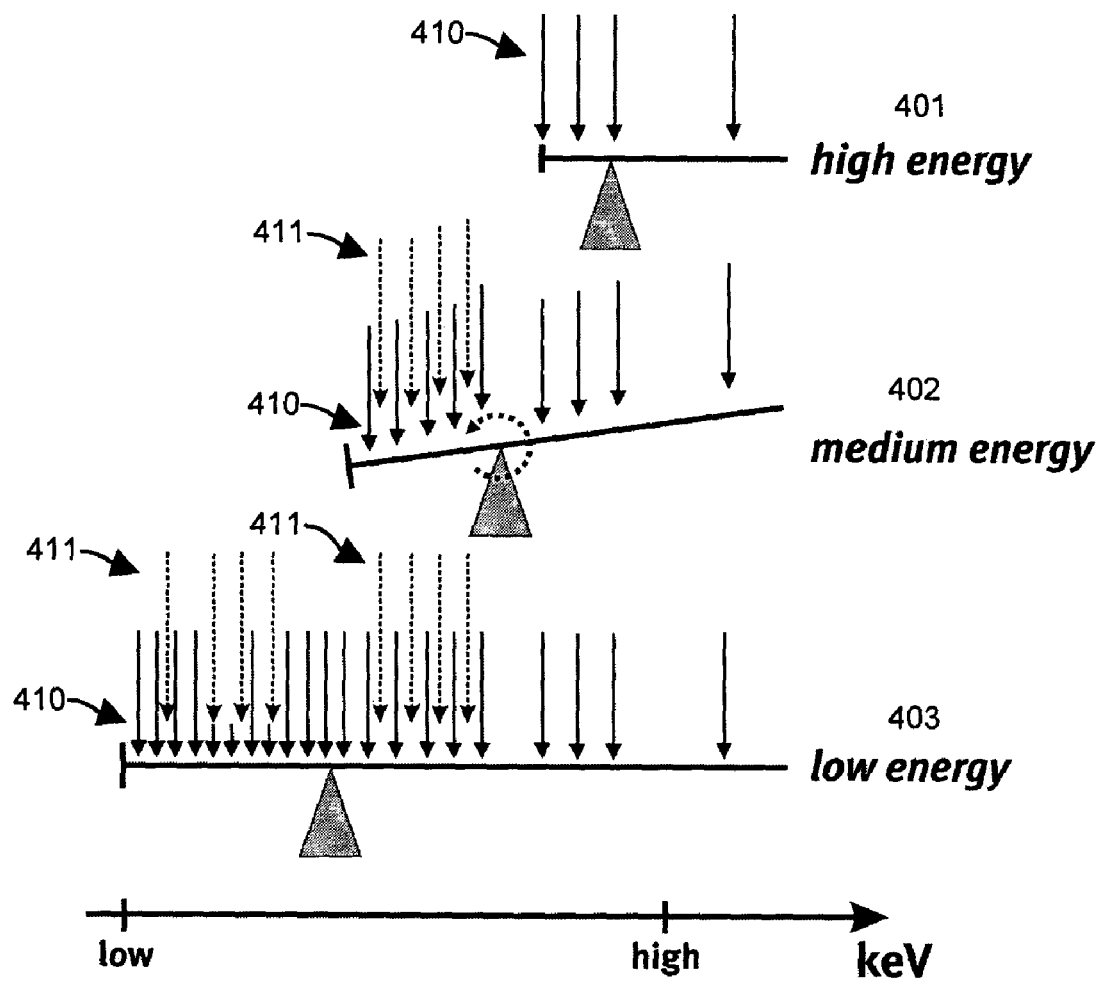
FIG. 10 illustrates background radiation with the addition of artificial radiation that produces an unbalanced state with scattered energies favoring the middle energy range as measured by the NBR processor used by embodiments of this invention.

FIG. 10 depicts an example of an upset balance condition with scattered energies from artificial radiation 411 that creates an unbalanced condition in the medium energy range 402 as opposed to the higher or lower energy ranges 401 or 403. In this example, the artificial radiation 411 effecting the medium energy NBR channel 402 falls outside of the acceptable limits causing the NBR processor 195 to produce an NBR alarm for a traffic way 112, while the low and high energy channels 401 and 403 would remain within their balance limits.

One phenomenon about the NBR processing technique used by embodiments of this invention is that NORM activity 410 does not upset the NBR balances, while artificial or man-made materials producing artificial radiation 411 do. The Compton Scattering pattern differences between these two types of sources are sufficiently separated allowing this NBR technique to work. Since NBR channels do not look solely for an increase count rate but rather an increase in one part of the spectrum compared to another, the net increase required to reliably produce an alarm is significantly less when compared to traditional counting methodologies.

NBR also provides the ability to process the data in real time. No post processing is required therefore alarms are posted immediately. The large area plastic detectors 137 further facilitate this real time process by producing sufficient counts to permit good statistical evaluations.

NBR is not affected by suppression of the background whenever a vehicle 115 attenuates background during the counting process. Traditional counting techniques require very sophisticated counting methodologies to lower the alarm limit which are referenced to background to follow the variable lowered backgrounds imposed upon the system due to shielding of the vehicle. Such conventional systems must essentially guess what the true background reduction truly is in order to set an alarm limit above the new estimated background. The difficulty aside from differing vehicle geometries and shielding properties arises when the vehicle additionally contains a real source, which in reality should set off an alarm. Since the variability of shielding configurations and sources are too numerous to fully characterize every possible scenario, these very complicated conventional methods cannot be 100% certain whether the perceived lowered backgrounds contain measurable materials of concern. The NBR counting channels 401 through 403 utilized by embodiments of this invention overcome this deficiency and eliminate the need for this level of complication all together since embodiments of the invention are not impacted by self-shielding nor are they required to provide such shielding, thus saving costs and reducing installation time and system complexity since detectors may be shared between traffic ways 112.

Figure 11:
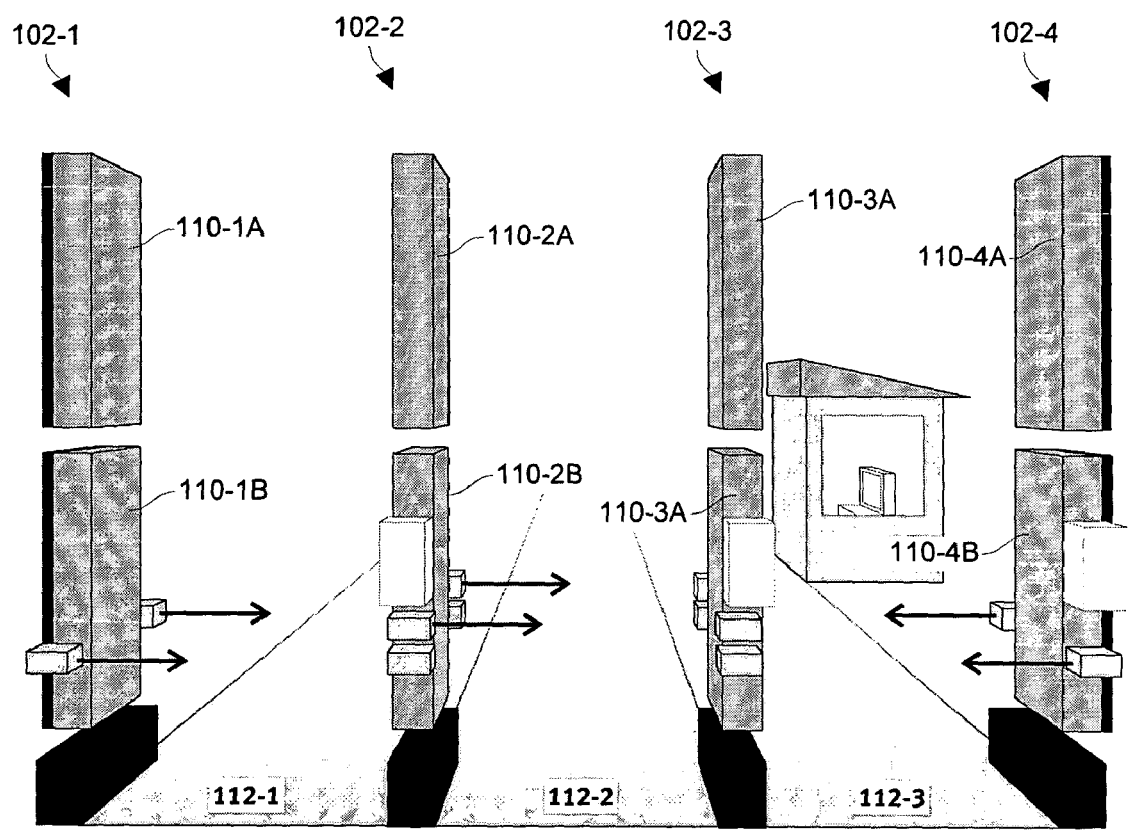
FIG. 11 illustrates an embodiment of the invention with stacked radiation detector assemblies.

FIG. 11 illustrates an alternative embodiment of the invention in which the number of radiation detector assemblies is multiplied by P, where P is an integer multiple indicating how many detector assemblies are to be positioned relative to one another (i.e., stacked or otherwise disposed in a planar arrangement such as on top of one another) to obtain a desired height requirement for detecting radiation sources in vehicles that extend that the height requirement. In this example, the traffic ways M=3 and each radiation detector installation area 102-1 through 102-4 includes multiple (P=2 in this example) radiation detector assemblies 110 stacked on top of one another in order to achieve a height factor that accommodates the geometry of the largest vehicle 115 that is anticipated to pass through each traffic way 112. In other words, if a single detector assembly 110 provides a vertical coverage area of, for example, six to eight feet in height, this alternative configuration of the invention provides multiple detector assemblies 110-1A and 110-1B at the radiation detector installation area 102-1, 110-2A and 110-2B at the radiation detector installation area 102-2 and so forth and each detector assembly 110 is operable in the manner explained herein. By stacking detector assemblies 110 on top of each other, this embodiment provides vertical coverage and detection capability for vehicles standing over the six to eight feet height detection area limit of the single detector assembly 110. It is to be understood that the six to eight feet limit is used by way of example only and the vertical detection capability of a single individual radiation detector assembly 110 and the number of stacked detector assemblies (two in this example) is not limited to this illustrated example.

Figure 12:
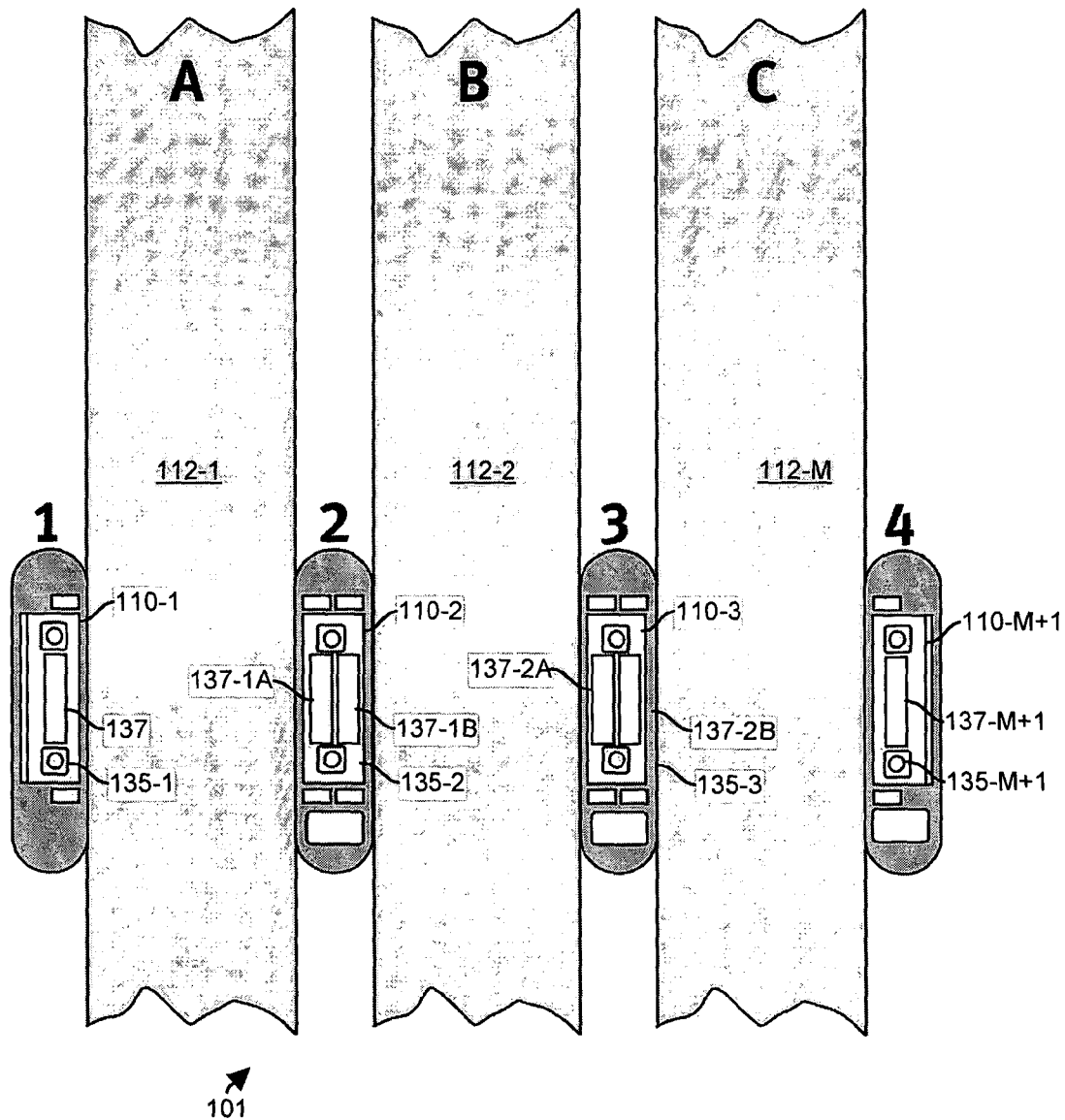
FIG. 12 illustrates an alternative embodiment of the invention which provides additional detector redundancy in which back to back detectors are used as shielding for each other.

FIG. 12 illustrates an alternative embodiment of the invention in which detector assemblies 110 positioned between adjacent traffic ways 112 include duplicate Gamma radiation detectors. The advantage of such configuration is that compared with conventional systems with individual detectors the count rate detected by both detectors (e.g., 137-1A and 137-1B) is approximately doubled and thus the same statistical significance is achieved in essentially half the time. This allows the monitoring of faster vehicles or alternatively the use of smaller detectors. Additionally since one detector (e.g., 137-1A) uses the other detector (e.g., 137-1B) as shielding from the other side (e.g., from background radiation in traffic way 112-2), an indication of from which lane 112 the radiation is originating can be derived on the level of an individual controller, while in conventional Type A systems a central computer coupling all controllers is required to make such a decision. In other words, on a lane by lane basis, a controller 120 itself can make a determination if a traffic way 112 contains a radiation source 118 without the help of correlation of all controller output by a central computer 150.

In particular, in the illustrated embodiment, the radiation detector assemblies 110-2 and 110-3 each contain two radiation detectors 137-1A and 137-1B (within the radiation detector assembly 110-2) and 137-2A and 137-2B (within the radiation detector assembly 110-3). In this configuration, the duplicate radiation detector assemblies A and B are positioned back to back such that each radiation detector assembly 137 provides some shielding effects to the corresponding radiation assembly 137 adjacent thereto. In this way, as compared to conventional Type A systems with individual detector assemblies for each traffic way or lane, significant cost savings in respect to the non-duplicated stanchions, Neutron detectors, and enclosures are achieved in combination with higher performance of the consolidated Gamma detector.

Figure 13:
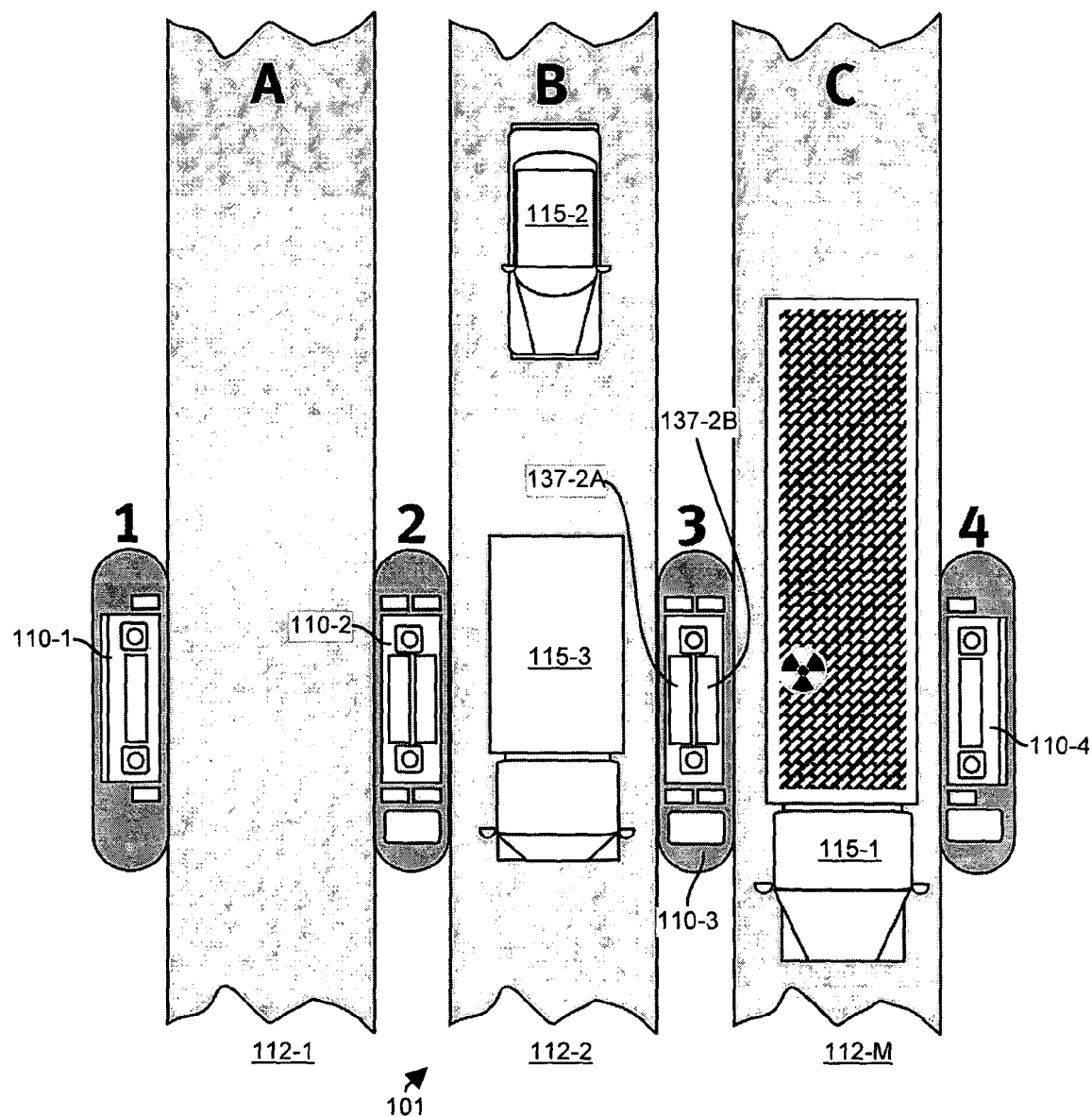
FIG. 13 illustrates an example traffic scenario of the alternative embodiment of the invention of FIG. 12.

FIG. 13 illustrates an example of the radiation detector system 101 in operation and example of traffic scenario similar to that described above the respective FIG. 6. Notice that the difference between the configuration illustrated in FIG. 13 and that illustrated in FIG. 6 is that the radiation detector assemblies 110-2 and 110-3 disposed between adjacent traffic weighs 112 in FIG. 13 include duplicate radiation detectors 137-1A, 137-1B and 137-2A and 137-2B arranged in the back to back configuration such that each provides some shielding to the other for background radiation. No other shielding is provided between these detectors 137, as opposed to conventional Type A systems in which a lead shield would be provided. Accordingly, when, for example, the large truck 115-1 induces a vehicle shielding effect, this effect is minimized to some extent by the existence of the radiation detector 137-2B upon the adjacent radiation detector 137-2A. As a result of this arrangement, the change of the energy distribution caused by the artificial source in the truck 115-1 can be detected with nearly doubled counting statistics based on the signals from detectors 137-2A and 137-2B. Also, the controllers connected to these detectors can indicate that the direction of incidence of the artificial radiation was more from traffic way 112-3 than from 112-2.

Figure 14:
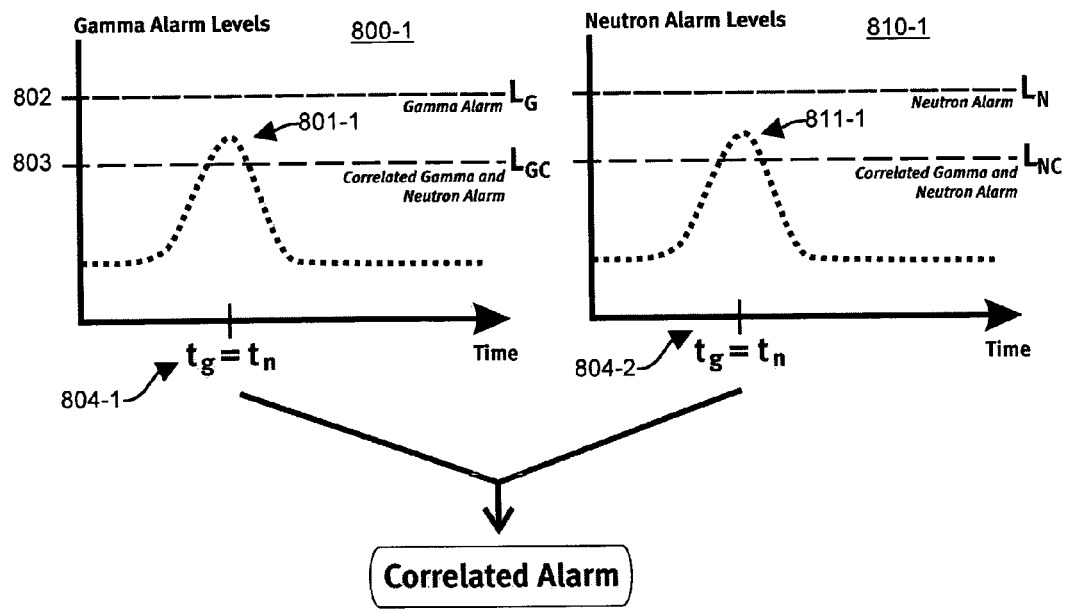
FIGS. 14 and 15 illustrate use of correlated alarm thresholds for Gamma radiation detectors and Neutron radiation detectors in accordance with an embodiment of the invention so as to reduce false alarm possibilities.
Figure 15:
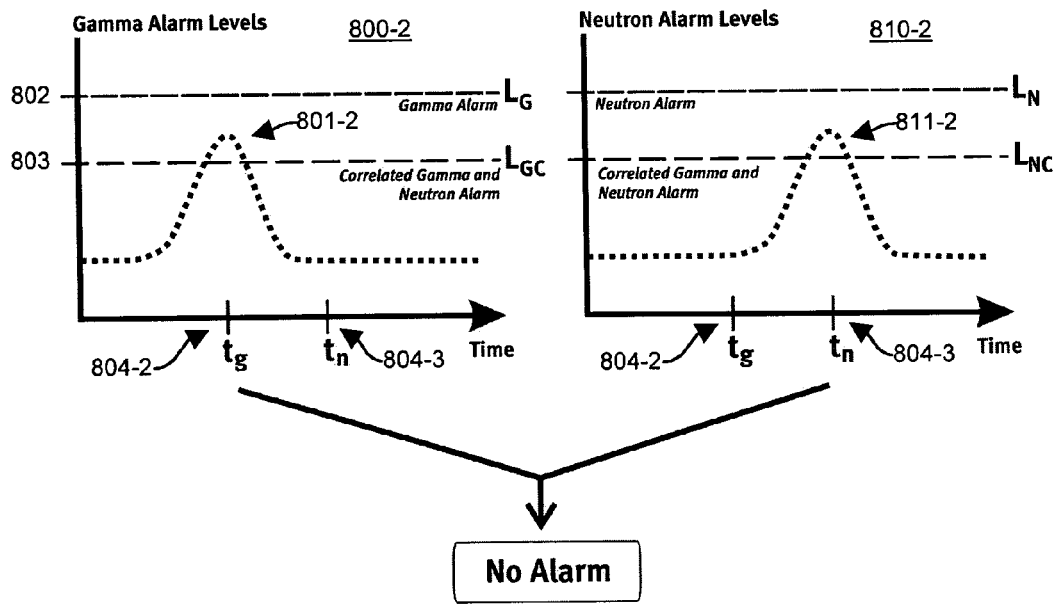

FIGS. 14 and 15 illustrate a further aspect of the previously-described embodiments of the invention which include both Gamma radiation detectors and Neutron radiation detectors. In particular, both FIGS. 14 and 15 show two radiation level graphs 800 and 810. The graphs 800-1 and 800-2 represent Gamma radiation levels while the graphs 810-1 and 810-2 represent Neutron radiation levels as detected at certain times $t_g$ and $t_n$ shown at locations 804-1 through 804-3 in the graphs. Peak levels 801 represent peak Gamma radiation detected, while peak levels 811 represent peak Neutron levels detected. On each graph 800 and 810, radiation level 802 on the vertical axis represents a threshold level of Gamma (for graphs 800) or Neutron (for graphs 810) radiation that, independent of other detected radiation levels, would cause embodiments of the invention to trigger an alarm condition. Radiation level 803 (below level 802 on the vertical axis of each graph 800 and 810) represents a correlated alarm threshold that indicated that if both Gamma and Neutron radiation levels that are concurrently detected when time $t_g$ is substantially the same as $t_n$ (as shown in FIG. 14 at 804-1, as opposed to FIG. 15), a correlated Gamma and Neutron alarm level has been reached. In other words, FIG. 14 represents a situation in which the system of the invention concurrently detects both Gamma and Neutron radiation levels (i.e., when time $t_g$ is substantially the same as $t_n$ at 804-1) and thus indicates a correlated alarm condition, even though neither radiation level peak 801-1 nor 811-1 by itself reached the peak levels 802 that would indicate an alarm condition for just one of Gamma or Neutron radiation levels. In contrast, FIG. 15 illustrates a no alarm condition since while the system of the invention detects both Gamma and Neutron radiation levels as indicated by peaks 801-2 and 811-2, the different times $t_g$ 804-2 and $t_n$ 804-3 indicate that such detections occur do not substantially coincide and thus no correlated alarm condition exits.

FIGS. 14 and 15 generally illustrate that if the setting of a certain alarm threshold $L_{GC}$ for the Gamma detectors would provide a false alarm probability of P1, and the setting of a certain alarm threshold for the Neutron detectors $L_{NC}$ would result in a false alarm probability of P2, it is possible to use the correlated event of an excess amount of artificial radiation detected by both detectors simultaneously above their respective alarm thresholds $L_{GC}$ and $L_{NC}$ in order to achieve a significantly reduced false alarm probability **P1\*P2. In this manner, in order to have an acceptable low total false alarm probability, significantly lower alarm thresholds for the correlated alarm compared to the Gamma only alarm level $L_{GC}$ or Neutron only alarm level $L_{NC}$ can be set. As an example, respective controllers associated with the two traffic ways adjacent to a radiation detector assembly can each be coupled to receive radiation signal data from the Gamma radiation detector and from the Neutron radiation detector linked to each common controller 120. In such cases, this controller is operable to time correlate gamma and neutron radiation levels as shown in the graphs in FIGS. 14 and 15** in order to have less false alarms respectively higher sensitivity for detection of radioactive isotopes such as Plutonium which emit both Neutron and artificial Gamma radiation.

Figure 16:
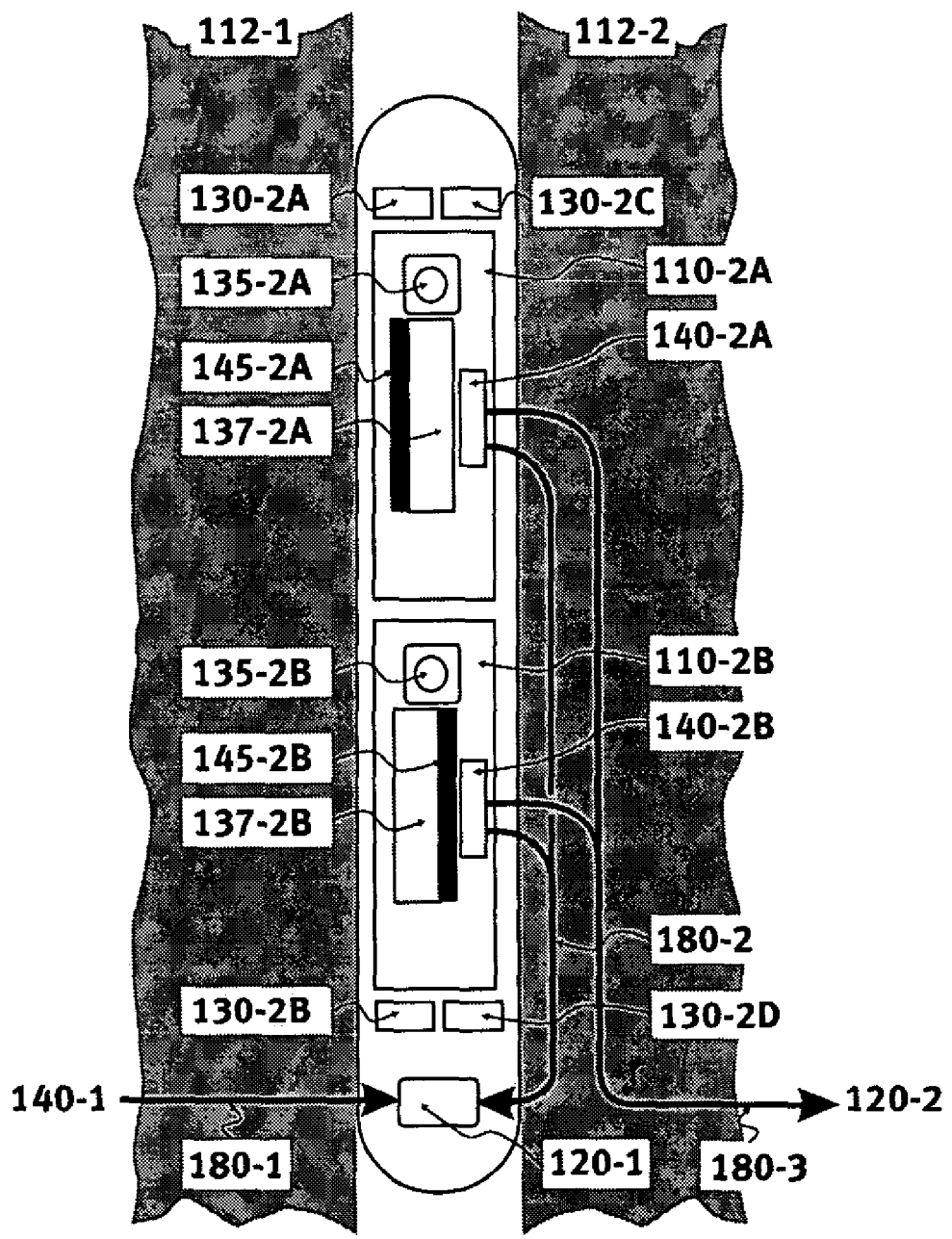
FIG. 16 illustrates an embodiment of the invention that includes shielded Gamma radiation detectors in separate detector assemblies that share two Neutron detectors.

FIG. 16 illustrates an embodiment of the invention that includes shielded Gamma radiation detectors 137-2A and 137-2B in separate detector assemblies between two adjacent traffic ways 112-1 and 112-2, but that share two Neutron detectors 135-2A and 135-2B. By providing such an embodiment, the system of the invention can reduce costs since fewer Neutron detectors 135 are required in configurations that provide separate detector assemblies for each traffic way 112. In other words, FIG. 16 is similar to that of existing installations of Type A systems, except that each detector assembly 110-2A and 110-2B in existing configurations would include two neutron detectors 135 each, for a total of four neutron detectors 135. Since only two Neutron detectors 135-2A and 135-2B are required using the system of the invention, significant cost can be saved while still achieving the desired results.

What is claimed is:

1. A radiation detection system capable of detecting a radiation source on or within traffic that can travel within M adjacent traffic ways, where M is an integer equal to or greater than a value of 2, the radiation detection system comprising:
   a set of (M+1) radiation detector assemblies, individual radiation detector assemblies of the set of (M+1) radiation detector assemblies respectively positioned at each of two sides of each of the M adjacent traffic ways;
   a set of M controllers, each controller associated with a respective traffic way of the M adjacent traffic ways, each controller coupled to the respective individual radiation detector assemblies positioned at the two sides of the traffic way to which that controller is associated, such that two controllers associated with two adjacent traffic ways couple to the individual radiation detector assembly positioned between those two adjacent traffic ways; and
   each controller being operable to receive a radiation signal produced from at least one radiation detector assembly coupled to that controller to identify a radiation source present in a traffic way adjacent to the at least one radiation detector assembly.

2. The radiation detection system of claim 1 wherein each radiation detector assembly positioned between adjacent traffic ways is operable to detect radiation from either of the two traffic ways adjacent to that radiation detector assembly.

3. The radiation detection system of claim 2 wherein each controller is operable to produce a controller output signal indicative of radiation detected by each radiation detector assembly coupled to that controller, and further comprising:
   a central computer system in communication with the set of M controllers to receive and process the controller output signals from each controller to thereby determine the presence of a radiation source and the traffic way in which the radiation source is present.

4. The radiation detection system of claim 3 wherein controller output signals from each controller provide:
   i) adjusted levels of radiation detected by the radiation detector assemblies coupled to that controller, the level adjusted to compensate for differences in artificial and non-artificial radiation detected by the radiation detector assemblies; and
   ii) an identity of each radiation detector assembly associated with the adjusted levels of radiation;
   the central computer system operable to correlate the adjusted levels of radiation from a plurality of radiation detector assemblies to identify patterns of correlated levels of radiation that indicate the existence of a radiation source within a specific traffic way of the M adjacent traffic ways.

5. The radiation detection system of claim 3 wherein the radiation detector assemblies are configured to detect a radiation source on or within vehicles traveling within the traffic ways, and the radiation detector assemblies positioned between adjacent traffic ways include:

unshielded radiation detectors exposed to background radiation and vehicle shielding from both adjacent traffic ways; and a natural background radiation rejection processor operable to adjust the levels of radiation detected by said unshielded radiation detectors so as to compensate for their absence of shielding.

6. The radiation detection system of claim 3 comprising:

a set of M traffic sensors respectively coupled to the set of M controllers, each traffic sensor associated with a respective traffic way and operable to produce a traffic signal when that traffic sensor detects traffic traveling in the traffic way to which that traffic sensor is associated; and wherein the controllers are operable to receive and process the traffic signals associated with their respectively coupled traffic sensors in conjunction with any radiation signals received from respectively coupled radiation detector assemblies to identify the traffic way in which a radiation source is traveling.

7. The radiation detection system of claim 6 wherein:

radiation detectors of radiation detector assemblies associated with a traffic way that has a neighboring traffic way are also coupled to the controller associated with the neighboring traffic way; and traffic sensors associated with a traffic way that has a neighboring traffic way are also coupled to the controller associated with the neighboring traffic way, such that in the event of failure of the controller associated with the traffic way associated with the traffic sensor, the controller associated with the neighboring traffic way can receive both a radiation signal and a traffic signal from the radiation detector and traffic sensors associated with the failed-controller traffic way to allow the controller of the neighboring traffic way to detect a radiation source in the failed controller traffic way.

8. The radiation detection system of claim 6 wherein the set of M traffic sensors include at least one of a speed sensor, an infrared sensor, a motion detector, and a light beam detector.

9. The radiation detection system of claim 3 wherein each radiation detector assembly positioned between adjacent traffic ways comprises:

a radiation detector operable to detect radiation from the traffic ways on either side of the radiation detector; and an amplifier module coupled to the radiation detector and operable to receive the detected radiation as an electrical signal from the radiation detector and to process the detected radiation to produce the radiation signal for transfer from the radiation detector assembly to the controllers coupled to that radiation detector assembly positioned between adjacent traffic ways.

10. The radiation detection system of claim 9 wherein each radiation detector assembly positioned between adjacent traffic ways includes a first radiation detector and a second radiation detector; and the amplifier module comprises a single shared preamplifier coupled to the first radiation detector and to the second radiation detector and operable to receive as electrical signals the radiation detected by the first and second radiation detectors, the single shared preamplifier further including a first radiation signal output interface and a second radiation output signal interface in communication with respective controllers associated with the two traffic ways adjacent to the radiation detector assembly.

11. The radiation system of claim 10 wherein the first radiation detector is a Gamma radiation detector and the second radiation detector is a Neutron radiation detector.

12. The radiation detection system of claim 11 wherein the Gamma radiation detector is an unshielded Gamma radiation detector.

13. The radiation detection system of claim 11 further including a third radiation detector that is also a Gamma radiation detector, and wherein the Neutron detector is coupled to both controllers associated with the traffic ways adjacent to the radiation detector assembly.

14. The radiation detection system of claim 13 wherein the first radiation detector and the third radiation detector are arranged back to back with each other and wherein each provides a shielding effect of background radiation with respect to the other.

15. The radiation detection system of claim 14 further including shielding disposed on a back side of each of the first and third radiation detectors to shield each of the first and third radiation detectors from background Gamma radiation in a direction of a back side of each of the first and third radiation detectors.

16. The radiation detection system of claim 11 wherein respective controllers associated with the two traffic ways adjacent to the radiation detector assembly are each coupled to receive radiation signal data from the Gamma radiation detector and from the Neutron radiation detector linked to a common controller, and wherein the respective controllers are operable to statistically correlate Gamma and Neutron radiation levels in order to have less false alarms for detection of radioactive isotopes which emit both Neutron and artificial Gamma radiation.

17. The radiation detection system of claim 9 wherein the amplifier module comprises a first preamplifier and a second preamplifier, each of the preamplifiers having a radiation signal output interface in communication with one of the controllers associated with each of the two traffic ways adjacent to the radiation detector assembly and operable to receive the detected radiation from the radiation detector and to process the detected radiation into respective radiation signals for transfer to the respective controller with which that preamplifier is in communication.

18. The radiation detection system of claim 9 further comprising:

a natural background radiation rejection processor operable in conjunction with the amplifier module to receive a level of radiation detected by the radiation detector and to apply a natural background rejection signal processing technique to the level of radiation to differentiate between changes in the radiation caused by non-natural radiation sources and changes in the radiation caused by naturally occurring radiation sources such that each of the detector assemblies positioned between adjacent traffic ways does not require shielding from background radiation.

19. The radiation detection system of claim 2 wherein the radiation detector assemblies positioned between adjacent traffic ways include unshielded Gamma radiation detectors.

20. The radiation detection system of claim 1 wherein the controllers operate independently of each other such that if one controller experiences a failure, at least one non-failed controller associated with at least one traffic way adjacent to a traffic way associated with the failed controller is operable to receive a radiation signal produced from the individual radiation detector assembly coupled to both the non-failed controller and the failed controller.

21. The radiation detection system of claim 1 wherein each radiation detector assembly positioned between two adjacent traffic ways comprises:
  a unshielded Gamma radiation detector operable to detect radiation from the traffic ways on either side of the radiation detector assembly.

22. The radiation detection system of claim 21 further comprising:
  a natural background radiation rejection processor operable in conjunction with the unshielded Gamma radiation detector to receive radiation signals from the radiation detector representative of Gamma radiation incident on the unshielded gamma radiation detector and to apply a natural background rejection signal processing technique to the radiation signals to differentiate between changes in radiation caused by non-natural radiation sources and changes in the radiation caused by naturally occurring radiation sources.

23. The radiation detector of claim 22 wherein each controller includes a natural background radiation rejection processor.

24. The radiation detection system of claim 1 wherein:
  the set of (M+1) radiation detector assemblies are disposed in a substantially planar manner with respect to each other to define a radiation detector array substantially perpendicular to the M adjacent traffic ways.

25. The radiation detection system of claim 24 wherein the radiation detector assemblies include an unshielded Gamma radiation detector that includes a natural background radiation rejection processor operable in conjunction with the at least one radiation detector in the radiation detector assemblies to receive levels of radiation detected by the radiation detector and to apply a natural background rejection signal processing technique to the radiation signals to differentiate changes in a level of radiation caused by non-natural radiation sources as compared to changes in a level of radiation caused by naturally occurring radiation sources, such that the detector assemblies positioned between adjacent traffic ways do not require shielding from background radiation.

26. The radiation detection system of claim 1 wherein every Nth radiation detector assembly includes a Neutron radiation detector coupled to controllers associated with the traffic ways adjacent to that radiation detector assembly, wherein N is an integer greater than 1.

27. The radiation detection system of claim 1 wherein the radiation detector assemblies are configured to detect a radiation source on or within vehicles traveling within the traffic ways, and comprising P radiation detector assemblies positioned at each of two sides of at least some of the M adjacent traffic ways, where P is an integer greater than one, each of said P radiation detector assemblies positioned on top of one another to obtain a desired height required for detecting radiation sources in vehicles that extend to a height above the radiation detection capability of a single radiation detection assembly.

28. A radiation detection system capable of detecting a radiation source, the radiation detection system comprising:
  a first radiation detector;
  a second radiation detector;
  a third radiation detector;
  the first radiation detector and second radiation detector defining a first traffic way;
  the second radiation detector and third radiation detector defining a second traffic way;
  a first controller coupled to the first radiation detector and coupled to the second radiation detector, the first controller operable to identify a radiation source within the first traffic way when at least one of the first radiation detector and the second radiation detector detect the radiation source passing through the first traffic way; and
  a second controller coupled to the second radiation detector and coupled to the third radiation detector, the second controller operable to identify a radiation source within the second traffic way when at least one of the second radiation detector and the third radiation detector detect the radiation source passing through the second traffic way.

29. The radiation detection system of claim 28 wherein the second radiation detector is an unshielded Gamma radiation detector.

30. The radiation detection system of claim 28 wherein each of the first and second controller include a respective natural background radiation rejection processor operable in conjunction with the controller to receive levels of radiation detected by the second radiation detector coupled to those controllers and to apply a natural background rejection signal processing technique to the levels of radiation to differentiate between changes in the radiation caused by non-natural radiation sources and changes in the radiation caused by naturally occurring radiation sources to identify which of the first and second traffic ways contains the radiation source.

31. A method for operating a radiation detection system to detect a radiation source on or within traffic that can travel within adjacent traffic ways, the method comprising:
  detecting a vehicle traveling in a traffic way of the adjacent traffic ways;
  receiving a radiation signal from an unshielded radiation detector disposed within a radiation detector assembly positioned between the adjacent traffic ways; and
  in response to detecting the vehicle and receiving the radiation signal, applying a natural background rejection signal processing technique to the radiation signal to differentiate between changes induced in radiation produced by naturally occurring radiation sources received by the unshielded radiation detector due to a position of the vehicle in relation to the unshielded radiation detector and changes in radiation caused by a non-natural radiation source that may be within the vehicle, the natural background rejection signal processing technique producing an output signal indicating whether or not the vehicle contains the non-natural radiation source; and
  wherein there are M adjacent traffic ways, where M is an integer equal to or greater than a value of 2, and wherein the radiation detection system comprises a set of (M+1) radiation detector assemblies, individual radiation detector assemblies of the set of (M+1) radiation detector assemblies respectively positioned at each of two sides of each of the M adjacent traffic ways and a set of M controllers, each controller associated with a respective traffic way of the M adjacent traffic ways, each controller coupled to the respective individual radiation detector assemblies positioned at the two sides of the traffic way to which that controller is associated, such that two controllers associated with two adjacent traffic ways couple to the individual radiation detector assembly positioned between those two adjacent traffic ways; and
  wherein receiving a radiation signal comprises:
  operating controllers of traffic ways adjacent to the radiation detector assembly containing the unshielded radiation detector that produced the radiation signal to each receive the radiation signal to identify the non-natural radiation source present in the vehicle in the traffic way adjacent to that radiation detector assembly.

32. The method of claim 31 comprising operating each radiation detector assembly positioned between adjacent traffic ways to detect radiation from either of the two traffic ways adjacent to that radiation detector assembly.

33. The method of claim 32 comprising operating the controllers independently of each other such that if one controller experiences a failure, at least one non-failed controller associated with at least one traffic way adjacent to a traffic way associated with the failed controller operates to receive a radiation signal produced from the individual radiation detector assembly coupled to both the non-failed controller and the failed controller.

34. The method of claim 32 comprising operating each controller to produce a controller output signal indicative of radiation detected by each radiation detector assembly coupled to that controller; and operating a central computer system in communication with the set of M controllers to receive and process the controller output signals from each controller to determine the presence of the non-natural radiation source and the traffic way in which the non-natural radiation source is present.

35. A method of operating a radiation detection system capable of detecting a radiation source on or within traffic that can travel within M adjacent traffic ways, where M is an integer equal to or greater than a value of 2, the method comprising:

operating a set of (M+1) radiation detector assemblies, individual radiation detector assemblies of the set of (M+1) radiation detector assemblies respectively positioned at each of two sides of each of the M adjacent traffic ways, such that at least one radiation detector assembly detects a radiation source traveling within at least one of the M adjacent traffic ways;

operating a set of M controllers, each controller associated with a respective traffic way of the M adjacent traffic ways, each controller coupled to the respective individual radiation detector assemblies positioned at the two sides of the traffic way to which that controller is associated, such that two controllers associated with two adjacent traffic ways couple to the individual radiation detector assembly positioned between those two adjacent traffic ways; and each controller operating to receive a radiation signal produced from at least one radiation detector assembly coupled to that controller to identify a radiation source present in a traffic way adjacent to the at least one radiation detector assembly.

* * * * *